United States Patent [19]

Hansen, Jr. et al.

[11] Patent Number: 4,757,153
[45] Date of Patent: Jul. 12, 1988

[54] SULFIDE, SULFINYL AND SULFONE DIPEPTIDE AMIDES

[75] Inventors: Donald W. Hansen, Jr., Chicago; Daniel R. Pilipauskas, Glenview; Michael Clare, Skokie, all of Ill.

[73] Assignee: G. D. Searle & Co., Chicago, Ill.

[21] Appl. No.: 882,796

[22] Filed: Jul. 14, 1986

Related U.S. Application Data

[63] Continuation-in-part of Ser. No. 829,389, Feb. 14, 1986, abandoned, which is a continuation-in-part of Ser. No. 765,885, Aug. 14, 1985, abandoned.

[51] Int. Cl.[4] .................. C07D 337/00; C07D 335/02; C07D 333/36; C07D 331/04; C07C 103/00; C07K 7/12
[52] U.S. Cl. ............................ 549/9; 549/28; 549/69; 549/88; 564/154; 558/413; 530/302
[58] Field of Search ............... 514/19; 530/302; 549/9, 549/28, 69, 88; 564/154; 558/413

[56] References Cited

U.S. PATENT DOCUMENTS

| | | | |
|---|---|---|---|
| 4,127,535 | 11/1978 | Coy et al. ........................ | 530/302 |
| 4,316,892 | 2/1982 | Jones ............................... | 530/302 |
| 4,407,746 | 10/1983 | Mazur et al. .................... | 530/302 |
| 4,579,841 | 4/1986 | Stewart et al. ................. | 514/19 |
| 4,603,121 | 7/1986 | Hansen, Jr. et al. ............ | 530/302 |

*Primary Examiner*—Delbert R. Phillips
*Attorney, Agent, or Firm*—Frank P. Grassler; Paul D. Matukaitis

[57] ABSTRACT

The invention relates to novel substituted tyrosyl alanine dipeptide amides of the formula:

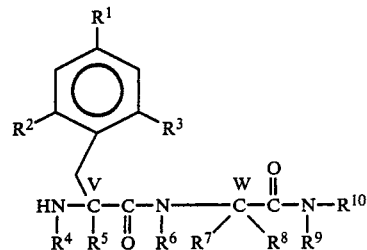

and the pharmaceutically acceptable acid addition salts thereof wherein $R^1$ is hydrogen, lower alkyl, hydroxy, lower alkoxy, $-O(CH_2)_n$phenyl with the phenyl optionally substituted by halogen, $-NO_2$, $-CN$, $-NH_2$ or lower alkyl wherein n is 1 to 4; $R^2$ and $R^3$ represent lower alkyl, halogen, or lower alkoxy, or either one of $R^2$ or $R^3$ is hydrogen and the other is lower alkyl, lower alkoxy or halogen; $R^4$, $R^5$, $R^6$, and $R^9$ may be the same or different and represent hydrogen, lower alkyl, cycloalkyl having 3 to 8 carbons, unsaturated lower alkyl, or $-(CH_2)_m$cycloalkyl with the cycloalkyl having 3 to 8 carbons and m is 1 to 4; $R^{10}$ is hydrogen or $-(CH_2)_p$-phenyl or with the phenyl optionally substituted with $-NH_2$, $-OH$, halogen, $-NO_2$, or lower alkyl or $-(CH_2)_p$ thienyl wherein p is 1 to 4; one of $R^7$ or $R^8$ is $-(CH_2)_f-S(O)_z-(CH_2)_q-CH_3$ where f is 1 to 3 and q is 0 to 3, z is 0, 1 or 2 and the other is hydrogen or lower alkyl, or $R^7$ and $R^8$ together with carbon w is

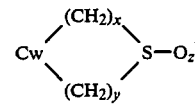

where x and y are independently 1 to 3 and z is 0, or 2. V represents an asymmetric carbon that may be recemic or have the D or L configuration; W represents an asymmetric carbon when $R^7$ and $R^8$ are not the same that may be recemic or have the D or L configuration.

The compounds of this invention are useful as analgesic and/or antihypertensive agents.

28 Claims, No Drawings

SULFIDE, SULFINYL AND SULFONE DIPEPTIDE AMIDES

This is a continuation-in-part of Ser. No. 829,389 filed Feb. 14, 1986, now abandoned which is a continuation-in-part of Ser. No. 765,885 filed Aug. 14, 1985, now abandoned.

SUMMARY OF THE INVENTION

This invention encompasses analgesic compounds of the formula:

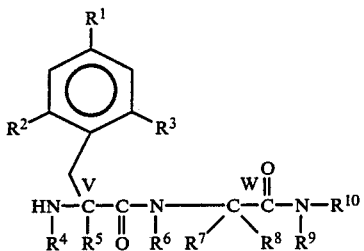

Formula I and the pharmaceutically acceptable acid addition salts thereof wherein $R^1$ is hydrogen, lower alkyl, hydroxy, lower alkoxy, —O(CH$_2$)$_n$phenyl with the phenyl optionally substituted by halogen, —NO$_2$, —CN, —NH$_2$ or lower alkyl wherein n is 1 to 4; $R^2$ and $R^3$ represent lower alkyl, halogen, or lower alkoxy, or either one of $R^2$ or $R^3$ is hydrogen and the other is lower alkyl, lower alkoxy or halogen; $R^4$, $R^5$, $R^6$, and $R^9$ may be the same or different and represent hydrogen, lower aklyl, cycloalkyl having 3 to 8 carbons, unsaturated lower alkyl, or (CH$_2$)$_m$ cycloalkyl with the cycloalkyl having 3 to 8 carbons and m is 1 to 4; $R^{10}$ is hydrogen or —(CH$_2$)$_p$-phenyl or with the phenyl optionally substituted with —NH$_2$, —OH, halogen, —NO$_2$, or lower alkyl or —(CH$_2$)$_p$ thienyl wherein p is 1 to 4; one of $R^7$ or $R^8$ is —(CH$_2$)$_f$—S(O)$_z$—(CH$_2$)$_q$—CH$_3$ where f is 1 to 3 and q is 0 to 3, z is 0, 1 or 2 and the other is hydrogen or lower alkyl, or $R^7$ and $R^8$ together with carbon w is

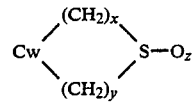

where x and y are independently 1 to 3 and z is 0, 1 or 2. V represents an asymmetric carbon that may be racemic or have the D or L configuration; W represents an asymmetric carbon when $R^7$ and $R^8$ are not the same that may be racemic or have the D or L configuration.

A preferred embodiment of the invention is compounds of the formula

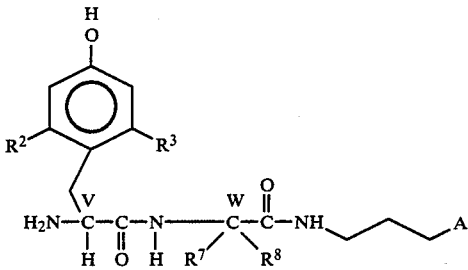

and the pharmaceutically acceptable acid addition salts thereof, wherein A is phenyl, thienyl, or cyclohexyl; wherein $R^2$ and $R^3$ are methyl; and wherein one of $R^7$ or $R^8$ is —(CH$_2$)$_f$—S(O)$_z$—(CH$_2$)$_q$—CH$_3$ where f is 1 to 3 and q is 0 to 3, z is 0, 1 or 2 and the other is hydrogen or lower alkyl, or $R^7$ and $R^8$ together with carbon w are

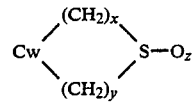

where x and y are independently 1 to 3 and z is 0, 1 or 2.

V represents an asymmetric carbon that may be racemic or have the D or L configuration; W represents an asymmetric carbon when $R^7$ and $R^8$ are not the same that may be racemic or have the D or L configuration.

In the context of this invention and the definition of $R^1$ through $R^{10}$ lower alkyl means straight or branched chain alkyls having 1 to 6 carbon atoms such as methyl, ethyl, propyl, isopropyl, butyl, iso-butyl, pentyl, and isomers thereof, and hexyl and isomers thereof.

Lower alkoxy means alkoxy having 1 to 6 carbon atoms where the alkyl moiety are as described above for lower alkyl.

Halo refers to chloro, fluoro, bromo and iodo.

FIELD OF THE INVENTION

The present invention relates to novel dipeptide amides. In particular, it provides novel dipeptide derivatives of Formula 1 which are useful as analgesic or antihypertensive agents.

BACKGROUND OF THE INVENTION

In 1975, a pentapeptide, methionine enkephalin, was reported by Hughes et al., *Nature*, 258, 577 (1975). This peptide is found in many areas of the brain where it appears to act as a neurotransmitter or neuromodulator in a central pain-suppressant system. The natural peptide binds stereospecifically to partially purified brain opiate receptor sites, see for example, Bradberry et al., *Nature*, 260, 793 (1976). The natural peptide is also highly active in bioassays for opiate activity but exhibits only weak, fleeting analgesic activity when injected directly into the brain of the rat, see for example, Belluzi et al., *Nature*, 260, 625 (1976)

In order to overcome the lack of in vivo activity, a number of investigators have made numerous modifications in the methionine enkephalin structure, such as substituting the glycine in the 2-position with a D-amino acid, N-methylation of the L-tyrosine, substituted the 4-phenylalanine with, for example, methyl or halo, modifying the C-terminus, etc., to produce enkephalin derivatives of varying properties and potencies.

Kiso, et al., "Peptide Chemistry 1981,": 65–70, Protein Research Foundation, Osaka, Japan (1982), disclosed the synthesis and activity of short chain enkephalin-like peptides, among them tripeptide and dipeptide alkylamides such as N-methyl tyrosine (D) methionine sulfoxide glycine-methylphenethylamide (2) and tyrosine-(D) methionine sulfoxide phenylpropyl amide (3).

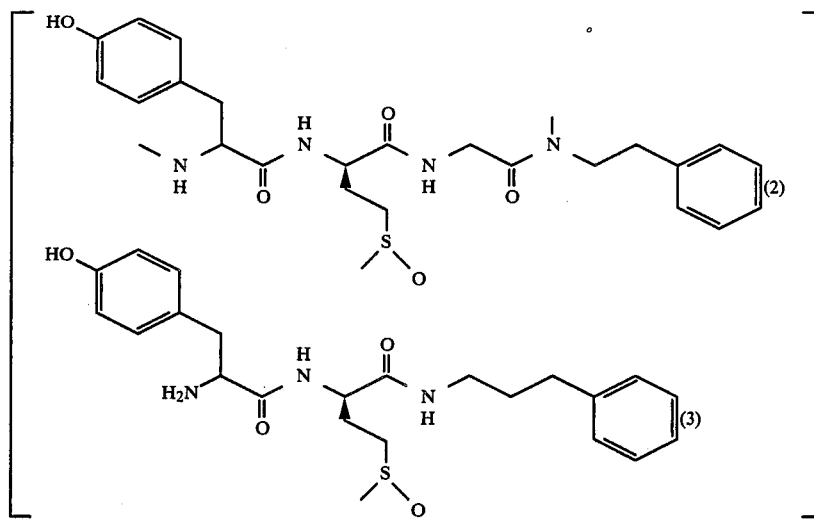

Vavrek, et al., Peptides 2, 303, 1981 disclosed analogs of enkephalin, among them the dipeptide tyrosine-D-alanine-phenylpropylamide (Tyr-(D) Ala-PPA) (4).

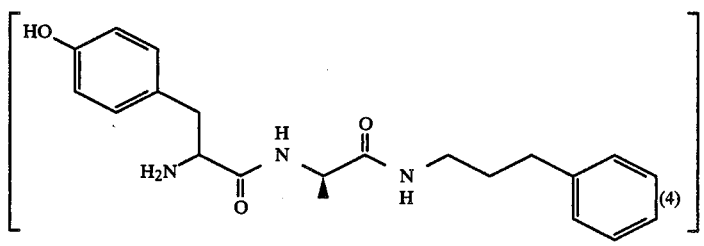

The compounds of this invention have unexpected and surprisingly superior properties when compared to the Vavrek compound. The present invention provides new enkephalin derivatives which show improved potency as analgesic agents by both oral and parenteral routes of administration. Additionally, U.S. Pat. No. 4,316,892 relates to certain derivatives of methionine enkephalin derivatives useful as analgesic agents.

DESCRIPTION OF THE SPECIFIC EMBODIMENTS

The compounds described in this invention and illustrated in Examples 1-68 are synthesized by either of two procedures illustrated in Scheme I Route A and Scheme II Route B. Many of the compounds can be prepared by either route with the principal difference being the reaction sequence.

Route A in Scheme I and Route B in Scheme II illustrate two methods for making compounds of this invention. In Route A a blocked amino acid derivative X is reacted with a dialkyl amine XI by mixed anhydride coupling and the blocking group is removed by acid hydrolysis to provide amide XII. A blocked tyrosine derivative XIII is reacted with amide XII by the mixed anhydride method to provide XIV which is separated into diastereomers, which are separately deblocked to provide compounds of formula I.

In Route B Scheme II the ester of the amino acid derivative is coupled with XIII by mixed anhydride coupling to provide ester XVI. This ester XVI is separated into diastereomers. For example, if XV is a D amino acid derivative and XIII is a DL tyrosine derivative, the DD and LD diastereomers are provided. The appropriate dialkylamine is then coupled to the separated diastereomer of XVII, and the product is deblocked to provide the compounds of Formula I.

In Schemes I and II Boc refers to tertiary butoxy carbonyl and $R^1$ through $R^{10}$ are as previously defined. Diastereomers are separated by standard techniques such as crystallization of column chromatography.

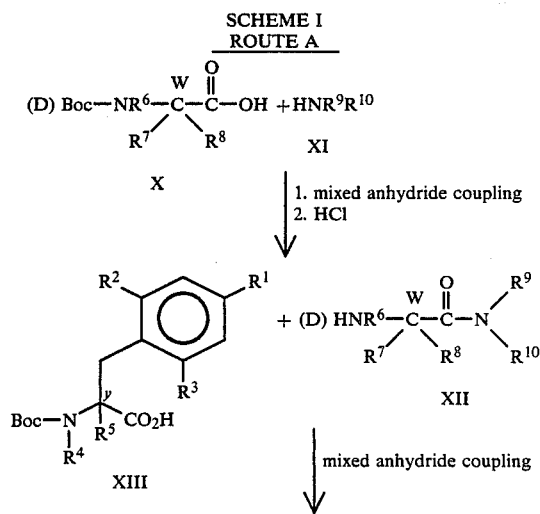

SCHEME I
ROUTE A

-continued
SCHEME I
ROUTE A

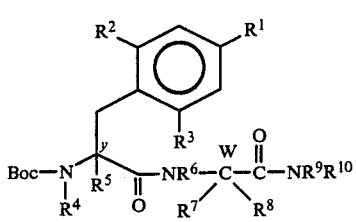

XIV separate diastereomers

LD      DD deblock    deblock

Compounds of Formula I

SCHEME II
ROUTE B

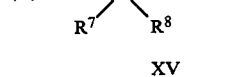

XIII

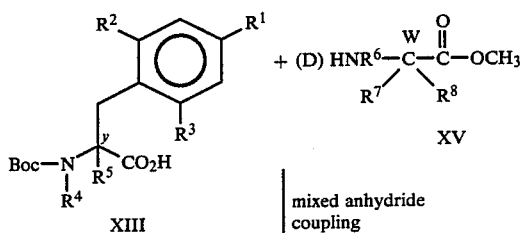

XV mixed anhydride coupling

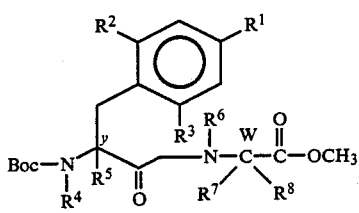

XVI 1. separate diastereomers
2. saponify

Diastereomer DD      Diastereomer LD

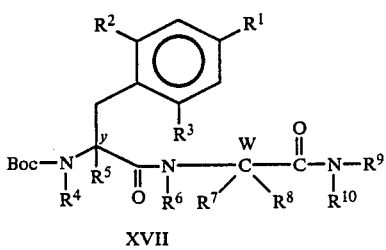

XVII

-continued
SCHEME II
ROUTE B

Mixed anhydride
coupling
with NHR$^9$R$^{10}$
(I)

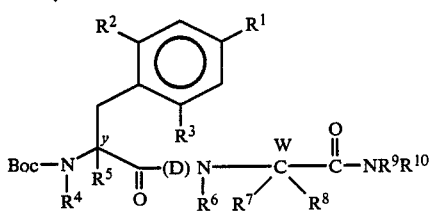

Deblock

Compounds of Formula I

The following tests indicate the analgesic properties of the compounds of the invention.

*Writhing assay.* Male Charles River albino mice (CD-1/HAM/1LR) weighing between 20 and 30 grams were used. Thirty minutes after subcutaneous or intragastric administration of the test compound (0.1 ml/10 gram body weight), 0.025% (w/v) phenylbenzoquinone was injected intraperitoneally (0.1 ml/10 gram body weight). Five minutes later, each mouse was placed in a large glass beaker and the number of writhes that occurred in the subsequent ten minutes is counted. A writhe consisted of dorsoflexion of the back, extension of the hindlimbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if the number of writhes in the drug treatment group was significantly less than the number of writhes in the saline treatment group as determined by a one-way analysis of variance. If the initial test dose of 10 mg/kg inhibited writhing in greater than 6 of 10 mice, the effect of additional doses was evaluated and an ED$_{50}$ value was calculated using a maximum likelihood function.

Opiate Binding Assay. The test compounds were evaluated for their ability to displace the binding of $^3$H-Naloxone to opiate receptors isolated from rat brain. Male rats [Crl: CD(SD)BR] obtained from Charles River Laboratories (Portage, MI) were sacrificed by cervical dislocation. A purified homogenate of receptor membranes was prepared from the brains according to the method described by Chang and Cuatrecasas. (K.-J. Chang and P. Cuatrecasas. Multiple Opiate Receptors: Enkephalins And Morphine Bind To Receptors Of Different Specificity. *J. Biol. Chem.* 254, 2610–2618 (1979).) The brains were homogenized in 10 volumes of 0.32M sucrose and centrifuged twice at 6,000xg for 15 minutes. Following centrifugation of the supernatants at 40,000xg for 30 minutes, the pellets were resuspended in 5 mM tris-HCl, and centrifuged at 6,000. The supernatant was centrifuged at 40,000xg. The resuspension in 5 mM Tris-HCl was repeated twice. The final pellet was resuspended in 2 volumes of 50 mM tris HCl (pH 7.4).

The homogenate was assayed for protein content according to the method of Itzhaki and Gill (R. F. Itzhaki and D. M. Gill. A Micro-Biuret Method for Estimating Proteins. *Anal. Biochem.* 9, 401–410 (1964)).

The binding of the test compounds to the receptor membrane preparation was measured using a modification of the method of Pert and Snyder (C. B. Pert and S. H. Synder. Properties of Opiate-Receptor Binding in Rat Brain. *Proc. Natl. Acad. Sci.* 70, 2243–2247 (1973)). The receptor assay was run using final concentrations of 1 nM $^3$H-Naloxone and of tissue homogenate (0.5 mg/ml of homogenate protein. Levorphanol ($1 \times 10^{-5}$M) was used as the displacer for non-specific binding. Final concentration of the test compounds was $10^{-5}$M. The assay was run in 0.05M tris HCl (pH 7.4). Total assay volume was 1.0 ml.

Samples were incubated at 25° C. for 60 min., filtered over Whatman GF/C glass fiber filters, and rinsed twice with 4 ml washes of ice-cold buffer. The filters were air-dried at 50° C. for 30 min. After drying 10 mls of PCS was added to the vial and the radioactivity determined using a Tracor Analytic Mark III liquid scintillation counter with a counting efficiency of 48%.

The IC$_{50}$ values, the concentration of the test compounds which inhibited $^3$H-Naloxone specific binding to the opiate receptor by 50%, were obtained from log-logit plots of concentration-response curves.

Analgesic properties are illustated in Table 1.

TABLE 1

| | ANALGESIC PROPERTIES | | |
|---|---|---|---|
| | Opiate[a] | Writing Mouse[b] | |
| Example | Binding | Subc. | Oral |
| 4 | $1.6 \times 10^{-8}$ | Inactive | Inactive |
| 8 | $9.6 \times 10^{-9}$ | Inactive | Inactive |
| 14 | $2.0 \times 10^{-10}$ | Active | Active |
| 15 | $1.6 \times 10^{-7}$ | Inactive | Inactive |
| 16 | $4.0 \times 10^{-10}$ | Active | Active |
| 17 | $9.6 \times 10^{-8}$ | Inactive | Inactive |

[a] = IC$_{50}$ expressed as moles/liter
[b] = Active refers to the effect of the screening dose (10 mg/kg).

The compounds can be administered in such oral dosage forms as tablets, capsules, pills, powders, granules, suspensions, or solutions. They may also be administered rectally or vaginally, in such forms as suppositories or bougies. They may also be introduced in the form of eyedrops, intraperitoneally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula 1 can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula 1 is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during column chromatography into diastereomers. The accompanying examples are used to illustrate two of the possible methods used to prepare the compounds of this invention.

ROUTE B

Example 1

N-[N-[(1,1-dimethylethoxy)carbonyl]-L-tyrosyl]-D-methionine, methyl ester

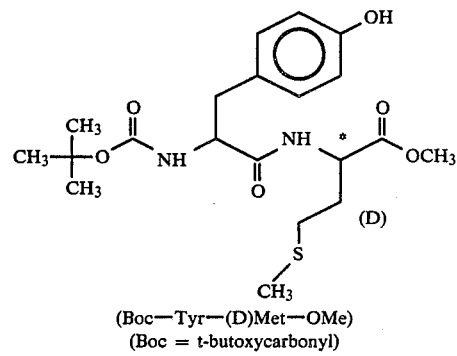

(Boc—Tyr—(D)Met—OMe)
(Boc = t-butoxycarbonyl)

To Boc-tyrosine (16.9 g, 60 mmol) in 150 ml of methylene chloride (CH$_2$Cl$_2$) cooled to 0° C. under an argon (Ar) atmosphere were added 6.6 ml (60 mmol) of N-methylmorpholine (NMM). After cooling this vigorously stirred solution to −78° C., 7.9 ml (60 mmol) of isobutylchloroformate (IBCF) were added to this reaction. The mixture was allowed to warm to 20° C. before it was again cooled to −78° and another 7.9 ml (60 mmol) of NMM were added. (D)Methionine methyl ester hydrochloride (12.0 g, 60 mmol) was then added to the reaction in a single portion. The mixture was allowed to warm to room temperature and stir for an additional 18 hours (h). After filtering the reaction through diatomaceous earth, the filtrate was washed 3 × 100 ml 0.5N potassium bisulfate (KHSO$_4$). The combined aqueous washed was extracted with CH$_2$Cl$_2$ (100 ml). The combined organic extracts were washed with 100 ml of brine, dried over sodium sulfate (Na$_2$SO$_4$) and stripped of all solvent under reduced pressure to produce the title product (25.1 g) as a light yellow glass. The material was used in subsequent reactions without further purification.

EXAMPLE 2

N-[N-[(1,1-dimethylethoxy)carbonyl]-L-tyrosyl]-D-methionine

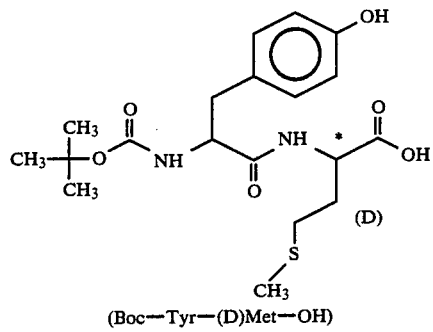

(Boc—Tyr—(D)Met—OH)

The title product of Example 1 (25.0 g, 58.6 mmol) dissolved in 150 ml of tetrahydrofuran (THF) was combined with a solution of potassium hydroxide (KOH, 7.7 g, 0.12 mmol) dissolved in 375 ml of water. After this reaction was stirred for 4 h, it was poured into a mixture of 2.5N KHSO$_4$ (400 ml) and CH$_2$Cl$_2$ (500 ml). The organic layer was separated and the aqueous (pH2) was extracted 3×100 ml of CH$_2$Cl$_2$. The combined organics were washed with 150 ml of brine, dried over Na$_2$SO$_4$, and stripped of all solvent under reduced pressure. The residue, after in vacuo drying, yielded 25 g of the title product as a white powder. This material was used without further purification.

EXAMPLE 3

N-[(1,1-dimethylethoxy)carbonyl]-L-tyrosyl-N-(3-phenylpropyl)-D-methioninamide

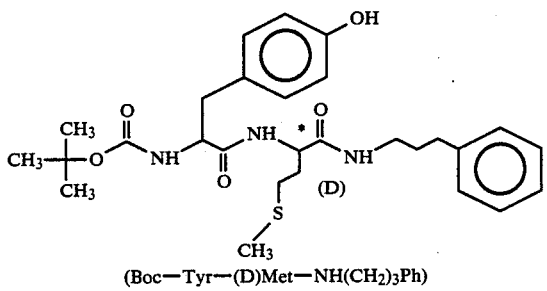

(Boc—Tyr—(D)Met—NH(CH$_2$)$_3$Ph)

The title product of Example 2 (7.4 g, 17.9 mmol) dissolved in 75 ml of CH$_2$Cl$_2$ was flushed with Ar and cooled to 0° C. N-methylpiperidine (NMP, 2.2 ml, 17.9 mmol) was added to the reaction before it was cooled to −78° C. and charged with 2.5 ml (17.9 mmol) of IBCF. The reaction was allowed to warm to −15°, maintained at this temperature for 15 min., cooled to −78°, and charged with 2.4 g (17.9 mmol) of 3 phenylpropyl amine (PPA). The crude product, obtained after a reaction work up by the method of Example 1, was chromatographed on a Waters prep 500 using a Porasil cartridge eluting with 2% to 3% ethanol (EtOH)/CH$_2$Cl$_2$. The title product was obtained as a white solid (4.54 g).

Optical rotation [α]$_D$ +22.3°; +80.9° (365) CHCl$_3$.

Analysis Calcd. for C$_{28}$H$_{39}$N$_3$O$_5$S (MW=529.71): C, 63.49; H, 7.42; N, 7.93. Found: C, 63.54; H, 7.41; N, 7.91.

EXAMPLE 4

L-tyrosyl-N-(3-phenylpropyl)-D-methioninamide, monohydrochloride

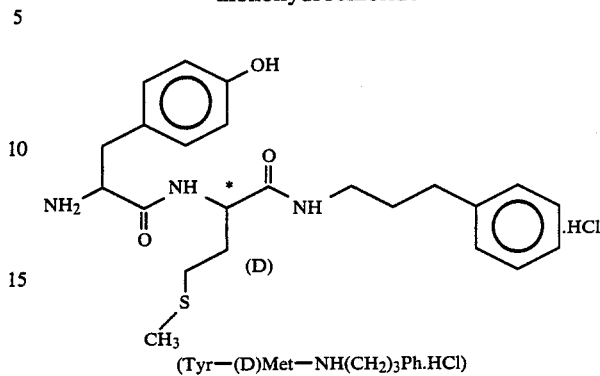

(Tyr—(D)Met—NH(CH$_2$)$_3$Ph.HCl)

The product of Example 3 (4.05 g, 7.6 mmol) was dissolved in 50 ml of acetic acid. To this solution was added 13 ml (76 mmol) of 6.0N HCl.dioxane. This solution was gently stirred under nitrogen (N$_2$) and at room temperature for 1 h before all the solvent was removed under reduced pressure. The resulting colorless oil residue on treatment with diethyl ether (Et$_2$O) solidified. This white title product salt was suction filtered, washed with Et$_2$O, and dried under vacuum (3.58 g).

Optical rotation [α]$_D$ +65.0°; +231.5° (365) methanol (MeOH).

Analysis Calcd. for C$_{23}$H$_{32}$N$_3$O$_3$SCl (MW=466.06): C, 59.28; H, 6.92; N, 9.02. Found: C, 59.07; H, 6.90; N, 9.07.

Example 5

L-tyrosyl-γ-(methylsulfonyl)-N-(3-phenylpropyl)-D-γ-aminobutanamide, monohydrochloride

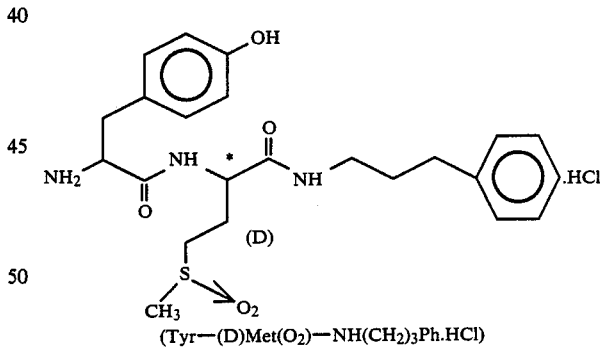

(Tyr—(D)Met(O$_2$)—NH(CH$_2$)$_3$Ph.HCl)

The title material of Example 4 (2.62 g, 5.6 mmol) dissolved in 50 ml of MeOH was charged with 6 ml (56 mmol) of 30% hydrogen peroxide. This mixture was brought to reflux and maintained for 30 minutes (min). After the reaction was cooled to room temperature, it was stirred an additional hour, and stripped of all solvent under reduced pressure. The residue was treated with Et$_2$O (150 ml) and the resulting title product, a white solid, was suction filtered, washed with Et$_2$O, and dried in vacuo (3.2 g).

Optical rotation [α]$_D$ +53.9°; +197.4° (315) MeOH.

Analysis Calcd. for C$_{23}$H$_{32}$N$_3$O$_5$SCl (MW=498.06): C, 55.47; H, 6.48; N, 8.44. Found: C, 55.93; H, 6.54; N, 8.45.

Example 6

N-[(1,1-dimethylethoxy)carbonyl]-L-tyrosyl-N-(3-phenylpropyl)-DL-methioninamide

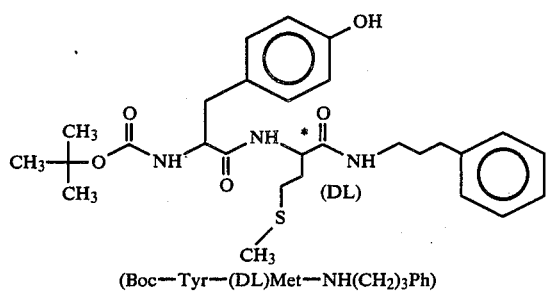

(Boc—Tyr—(DL)Met—NH(CH₂)₃Ph)

The title compound was prepared by the method of Example 3 from Boc-Tyr-(DL)Met which was obtained by the methods of Examples 1 and 2 substituting (DL)Met in place of (D)Met.

Analysis Calcd. for $C_{28}H_{39}N_3O_5S.\frac{1}{2}H_2O$ (MW=538.72): C, 62.42; H, 7.48; N, 7.80; 5.95. Found: C, 62.68; H, 7.34; N, 7.40, 6.06.

Example 7

L-tyrosyl-N-(3-phenylpropyl)-DL-methioninamide, monohydrochloride

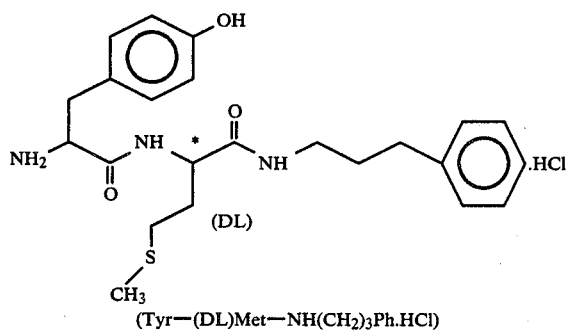

(Tyr—(DL)Met—NH(CH₂)₃Ph.HCl)

The title compound was prepared from the title material of Example 6 by the method of Example 4.

Optical rotation $[\alpha]_D$ +3.10°; +124.0° (365) MeOH. Analysis Calcd. for $C_{32}H_{32}N_3O_3SCl.\frac{1}{2}H_2O$ (MW=475.06): C, 58.15; H, 7.00; N, 8.85; S, 6.74. Found: C, 58.26; H, 6.95; N, 8.68; S, 7.00.

Example 8

L-tyrosyl-γ-(methylsulfonyl)-N-(3-phenylpropyl)-DL-α-aminobutanamide, monohydrochloride

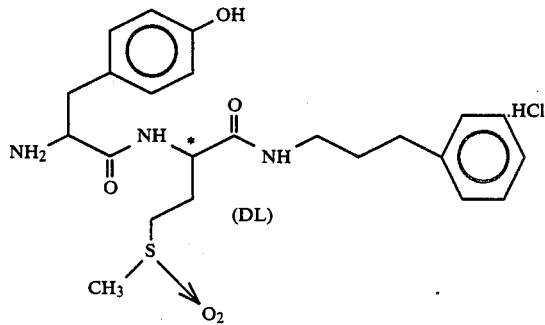

(Tyr—(D,L)Met(O₂)—NH(CH₂)₃Ph.HCl)

The title material was prepared from the title material of Example 7 by the method of Example 5.

Optical rotation $[\alpha]_D$ +26.4°; +110.4° (365) MeOH. Analysis Calcd. for $C_{23}H_{32}N_3O_5SCl.\frac{1}{2}H_2O$ (MW=507.06): C, 54.48; H, 6.56; N, 8.29; S, 6.32. Found: C, 54.54; H, 6.49; N, 8.23; S, 6.44.

Example 9

N-[N-[(1,1-dimethylethoxy)carbonyl]-2,6-dimethyl-DL-tyrosyl]-D-methionine, methyl ester

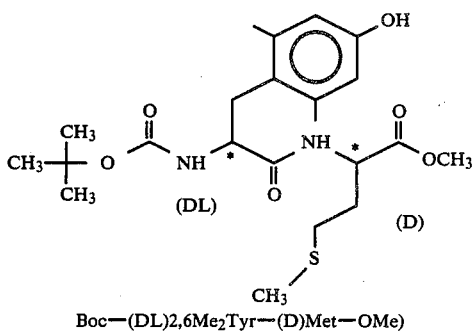

Boc—(DL)2,6Me₂Tyr—(D)Met—OMe)

The title compounds were prepared by the method of Example 1 using racemic t-butoxycarbonyl 2,6-dimethyltyrosine in place of Boc-Tyr. The product mixture of diastereomers were separated by fractional recrystallization from CH₂Cl₂/hexane.

Diastereomer A $[\alpha]_D$ +52.0° (MeOH).

Analysis Calcd. for $C_{22}H_{34}N_2O_6S$ (MW=454.58): C, 58.13; H, 7.54; N, 6.16; S, 7.05. Found: C, 57.79; H, 7.56; N, 6.25; S, 7.00.

Diastereomer B $[\alpha]_D$ +7.5° (MeOH).

Analysis Calcd. for $C_{22}H_{34}N_2O_6S$ (MW=454.58): C, 58.13; H, 7.54; N, 6.16. Found: C, 58.50; H, 7.64; N, 5.99.

Example 10

N-[N-[(1,1-dimethylethoxy)carbonyl]-2,6-dimethyl-L-tyrosyl]-D-methionine

Isomer-A

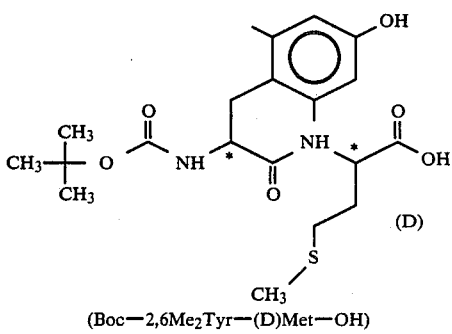

(Boc—2,6Me₂Tyr—(D)Met—OH)

The title material was prepared from diastereomer A of Example 9 by the method of Example 2.

Optical rotation $[\alpha]_D$ +39.1°; +122.7° (365) MeOH. Analysis Calcd. for $C_{21}H_{32}N_2O_6S$ (MW=440.55): C, 57.25; H, 7.34; N, 6.36; S, 7.28. Found: C, 57.18; H, 7.41; N, 6.00; S, 6.60.

Example 11

N-[N-[(1,1-dimethylethoxy)carbonyl]-2,6-dimethyl-D-tyrosyl]-D-methionine

Isomer-B

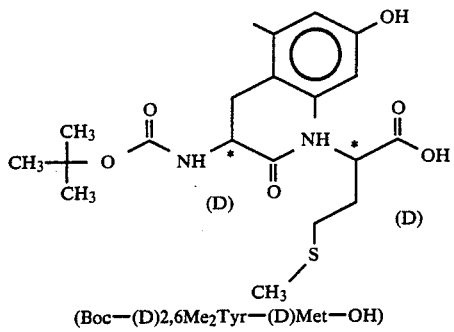

(Boc—(D)2,6Me₂Tyr—(D)Met—OH)

The title material was prepared from diastereomer B of Example 9 by the method of Example 2.

Optical rotation $[\alpha]_D$ +8.2°; +27.3° (365) MeOH.

Analysis Calcd. for $C_{21}H_{32}N_2O_6S$ (MW=440.55): C, 57.25; H, 7.32; N, 6.36; S, 7.28. Found: C, 57.64; H, 7.45; H, 6.12; S, 6.85.

Example 12

N-[(1,1-dimethylethoxy)carbonyl]-2,6-dimethyl-L-tyrosyl-N-(3-phenylpropyl)-D-methioninamide Isomer-A (Boc-2,6Me₂Tyr-(D)Met-NH(CH₂)₃Ph)

The title material was prepared from the title compound of Example 10 by the method of Example 3.

Optical rotation $[\alpha]_D$ +46.7°; +171.7° (365) CHCl₃.

Analysis Calcd. for $C_{30}H_{43}N_3O_5S$ (MW=557.82): C, 64.59; H, 7.79; N, 7.54; S, 5.75. Found: C, 64.09; H, 7.66; N, 7.41; S, 5.76.

Example 13

N-[(1,1-dimethylethoxy)carbonyl]-2,6-dimethyl-D-tyrosyl-N-(3-phenylpropyl)-D-methioninamide Isomer-B

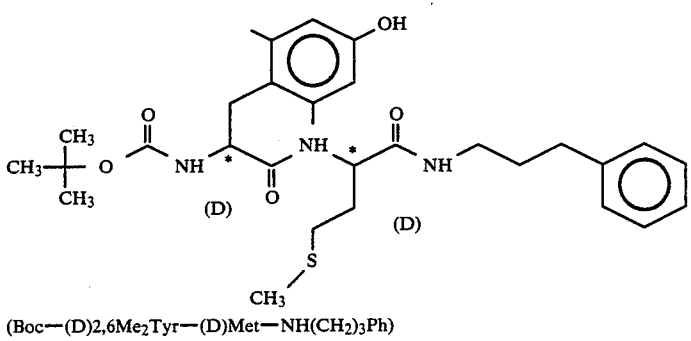

(Boc—(D)2,6Me₂Tyr—(D)Met—NH(CH₂)₃Ph)

The title product was synthesized from the title compound of Example 11 by the method of Example 3.

Optical rotation $[\alpha]_D$ −4.8°; −25.8° (365) CHCl₃.

Analysis Calcd. for $C_{30}H_{43}N_3O_5S$ (MW=557.75): C, 64.60; H, 7.77; N, 7.53; S, 5.75. Found: C, 64.50; H, 7.73; N, 7.32; S, 5.64.

Example 14

2,6-dimethyl-L-tyrosyl-N-(3-phenylpropyl)-D-methioninamide, monohydrochloride

Isomer-A

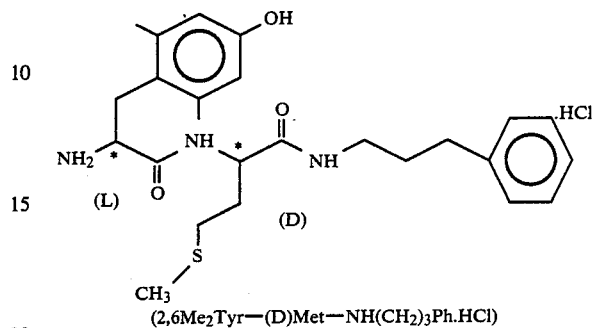

(2,6Me₂Tyr—(D)Met—NH(CH₂)₃Ph.HCl)

The title compound was synthesized from the title product of Example 12 by the method of Example 4.

Optical rotation $[\alpha]_D$ +115.2°; +411.4° (365) MeOH.

Analysis Calcd. for $C_{25}H_{36}N_3O_3SCl.\frac{1}{2}H_2O$ (MW=503.11): C, 59.63; H, 7.42; N, 8.35; S, 6.37; Cl, 7.04. Found: C, 59.63; H, 7.28; N, 8.10; S, 6.36; Cl, 7.35.

Example 15

2,6-dimethyl-D-tyrosyl-N-(3-phenylpropyl)-D-methioninamide, monohydrochloride

Isomer-B

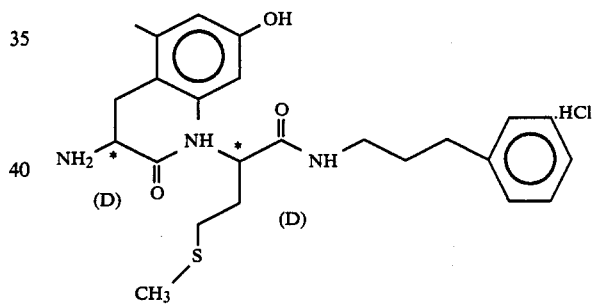

((D)2,6Me₂Tyr—(D)Met—NH(CH₂)₃Ph.HCl)

The title product was prepared from the title compound of Example 13 by the method of Example 4.

Optical rotation $[\alpha]_D$ −32.3°; −127.0° (365) MeOH.

Analysis Calcd. for $C_{25}H_{36}N_3SCl.\frac{1}{2}H_2O$ (MW=503.11): C, 59.63; H, 7.42; N, 8.35; S, 6.37; Cl, 7.04. Found: C, 59.45; H, 7.23; N, 8.29; S, 6.55; Cl, 8.23.

Example 16

2,6-dimethyl-L-tyrosyl-α-(methylsulfinyl)-N-(3-phenylpropyl)-D-α-aminobutanamide, monohydrochloride Isomer-A

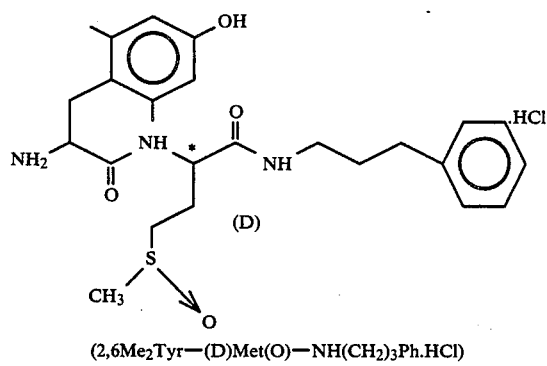

(2,6Me₂Tyr—(D)Met(O)—NH(CH₂)₃Ph.HCl)

The title compound from Example 14 (186 mg, 0.37 mmol) was dissolved in 1 ml of MeOH and 3 ml of H₂O. To this solution stirred under an Ar atmosphere at room temperature was added 1 ml of 30% hydrogen peroxide. After 1 h, the reaction was filtered, diluted with H₂O (30 ml), and lyopholized to give 133 mg of the title material.

Optical rotation $[\alpha]_D$ +96.2°; +343.8° (365) MeOH.

Analysis Calcd. for C₂₅H₃₆N₃O₄SCl.H₂O (MW=544.13): C, 55.18; H, 7.43; N, 7.72. Found: C, 55.18; H, 6.94; N, 7.77.

EXAMPLE 17

2,6-dimethyl-D-tyrosyl-γ-(methylsulfinyl)-N-(3-phenylpropyl)-D-α-aminobutanamide, monohydrochloride

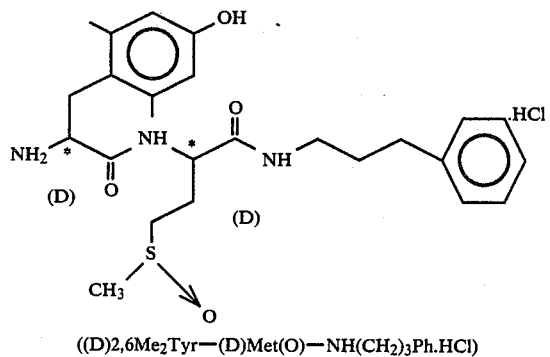

((D)2,6Me₂Tyr—(D)Met(O)—NH(CH₂)₃Ph.HCl)

The title compound was prepared from the title material of Example 15 by the method of Example 16.

Optical rotation $[\alpha]_D$ −33.2°; −118.3° (365) MeOH.

Analysis Calcd. for C₂₅H₃₆N₃O₄SCl (MW=510.15): C, 55.18; H, 7.43; N, 7.72; S, 5.89; Cl, 6.52. Found: C, 55.24; H, 7.01; N, 7.68; S, 6.01; Cl, 6.86.

ROUTE A

EXAMPLE 18

1,1-dimethylethyl [3-(ethylthio)-1R-[[(3-phenylpropyl)amino]carbonyl]propyl]carbamate

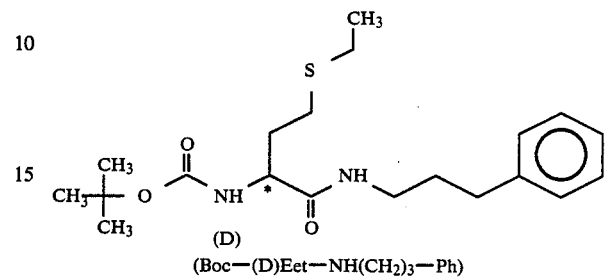

(Boc—(D)Eet—NH(CH₂)₃—Ph)

Boc-(D)Ethionine (Boc-(D)Eet 10 g, 38.0 mmol) dissolved in CH₂Cl₂ (70 ml) was cooled to 0° C. and NMM (5.0 ml. 45.6 mmol) was added. After cooling this vigorously stirred solution under an Ar atmosphere to −78° C., IBCF (5.9 ml, 45.6 mmol) was added. The reaction was allowed to warm slowly to 0° C. before it was again cooled to −78° and charged with 3-phenylpropylamine (6.2 g, 45.6 mmol). The mixture was warmed to room temperature, stirred for 24 h, and filtered. After diluting the filtrate with CH₂Cl₂, it was washed with 0.5N KHSO₄. The combined aqueous washes were extracted with CH₂Cl₂ and the combined organic layers were washed with brine, dried (Na₂SO₄), and stripped of all solvent. The residue title product, 9.8 g, was dried under vacuum and used in subsequent reactions without further purification.

Analysis Calcd. for C₂₀H₃₂N₂SO₃ (MW=380.55): C, 63.12; H, 8.48; N, 7.36; S, 8.43. Found: C, 63.08; H, 8.42; N, 7.37; S, 8.41.

EXAMPLE 19

2R-amino-4-(ethylthio)-N-(3-phenylpropyl)butanamide, monohydrochloride

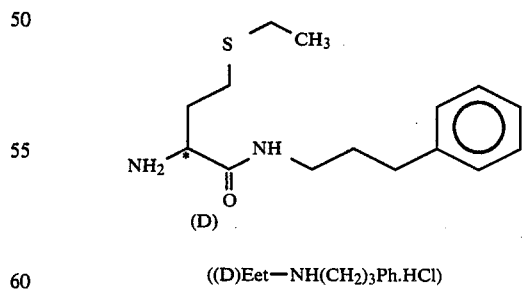

((D)Eet—NH(CH₂)₃Ph.HCl)

The title compound was synthesized from the title material of Example 18 by the method of Example 4.

Optical rotation $[\alpha]_D$ −13.3°; −55.0° (365) MeOH.

Analysis Calcd. for C₁₅H₂₅N₂OSCl (MW=316.89): C, 56.85; H, 7.95; N, 8.84; S, 10.12; Cl, 11.19. Found: C, 56.72; H, 8.28; N, 8.91; S, 10.25; Cl, 11.19.

EXAMPLE 20

N-[(1,1-dimethylethoxy)carbonyl]-2,6-dimethyl-DL-tyrosyl-S-ethyl-N-(3-phenylpropyl)-D-homocysteinamide

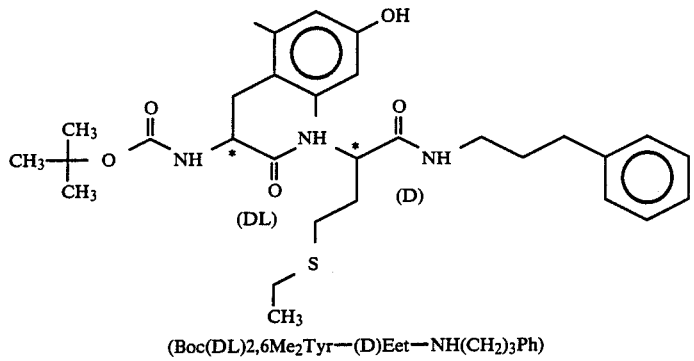

(Boc(DL)2,6Me₂Tyr—(D)Eet—NH(CH₂)₃Ph)

The title product mixture of diastereomers (isomer A and isomer B) were prepared by the method of Example 1 using the title material from Example 19 in place of (D)Met-OMe and racemic Boc-2,6Me₂Tyr in place of Boc-Tyr. The initially eluting material (isomer A) and the second eluting material (isomer B) were separated by pressure liquid chromatography (PLC) using 2% MeOH/CHCl₃ as eluent.

Diastereomer A $[\alpha]_D$ +7.4°; +30.7° (365) CHCl₃.
Analysis Calcd. for $C_{31}H_{45}N_3O_5S$ (MW=571.78): C, 65.12; H, 7.93; N, 7.35; S, 5.61. Found: C, 65.09; H, 7.90; N, 7.36; S, 5.76.

Diastereomer B $[\alpha]_D$ +46.4°; +185.5° (365) CHCl₃.
Analysis Calcd. for $C_{31}H_{45}N_3O_5S$ (MW=571.78): C, 65.12; H, 7.93; N, 7.35; S, 5.61. Found: C, 64.86; H, 7.83; N, 7.26; S, 5.61.

EXAMPLE 21

2,6-dimethyltyrosyl-S-ethyl-N--(3-phenylpropyl)-D-homocysteinamide, monohydrochloride

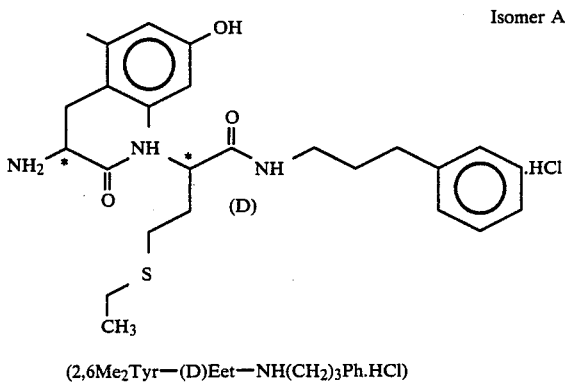

Isomer A (2,6Me₂Tyr—(D)Eet—NH(CH₂)₃Ph.HCl)

The title compound was prepared from the A-diastereomer of Example 20 by the method of Example 4.
Optical rotation $[\alpha]_D$ −59.6°, −225.3° (365) MeOH.
Analysis Calc. for $C_{26}H_{38}N_3O_3SCl$ (MW=508.13): C, 61.46; H, 7.54; N, 8.27; S, 6.31; Cl, 6.98. Found: C, 61.29; H, 7.54; N, 8.42; S, 6.46; Cl, 6.67

EXAMPLE 22

2,6-dimethyltyrosyl-S-ethyl-N-(3-phenylpropyl)-D-homocysteinamide, monohydrochloride

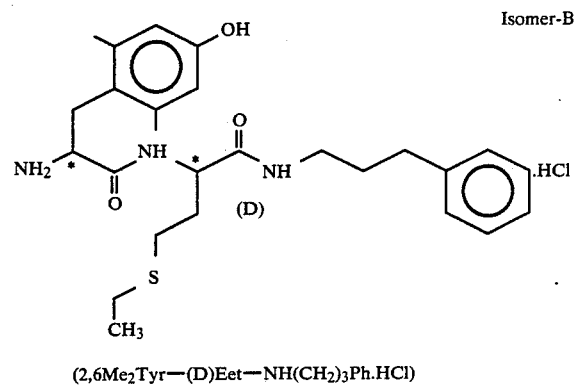

Isomer-B (2,6Me₂Tyr—(D)Eet—NH(CH₂)₃Ph.HCl)

The title compound was synthesized from the B diastereomer of Example 20 by the method of Example 4.
Optical rotation $[\alpha]_D$ +131.8°, +449.3°(365) MeOH.
Analysis Calc. for $C_{26}H_{38}N_3O_3SCl$ (MW=508.13): C, 61.46; H, 7.54; N, 8.27; S, 6.31; Cl, 6.98. Found: C, 61.08; H, 7.48; N, 8.48; S, 6.28; Cl, 6.94

EXAMPLE 23

2,6-dimethyltyrosyl-γ-(ethylsulfinyl)-N-(3-phenylpropyl)-D-α-aminobutanamide, monohydrochloride

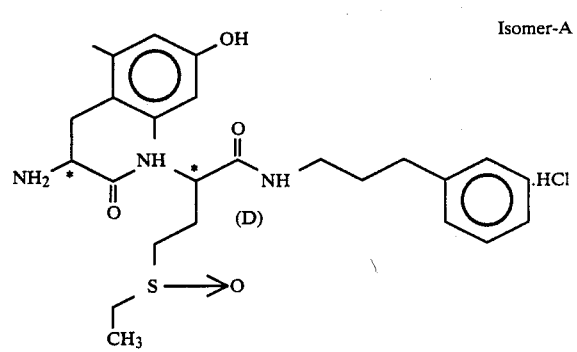

Isomer-A (2,6Me₂Tyr—(D)Eet—NH(CH₂)₃Ph.HCl)

The title compound was prepared from the product of Example 21 by the method of Example 16.
Optical rotation $[\alpha]_D$ −53.2°; −195.2°(365) MeOH.

Analysis Calc. for $C_{26}H_{38}N_3O_3SCl \cdot \frac{1}{2}H_2O$ (MW=533.12): C, 58.58; H, 7.37; N, 7.88; S, 6.01; Cl, 6.65. Found: C, 58.15; H, 7.02; N, 7.74; S, 5.73; Cl, 6.88.

EXAMPLE 24

2,6-dimethyltyrosyl-α-(ethylsulfinyl)-N-(3-phenyl-propyl)-D-α-aminobutanamide, monohydrochloride

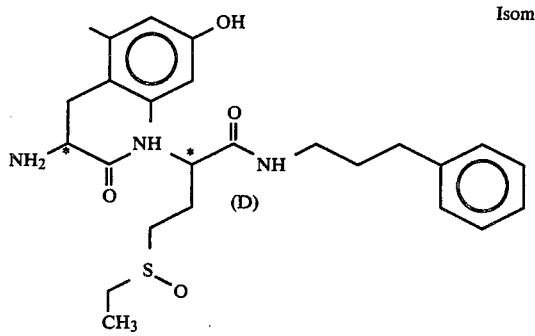

(2,6Me₂Tyr(D)Eet(O)—NH(CH₂)₃Ph.HCl)

The title compound is prepared from the product of Example 22 by the method of Example 16.

Optical rotation $[\alpha]_D$ +104.3°+362.7°(365) MeOH.

Analysis Calc. for $C_{26}H_{38}N_3O_4SCl \cdot \frac{1}{2}H_2O$ (MW=533.12): C, 58.58; H, 7.37; N, 7.88; S, 6.01; Cl, 6.65. Found: C, 58.55; H, 7.28; N, 7.80; S, 5.92; Cl, 7.03

EXAMPLE 25

2,6-dimethyltyrosyl-γ-(ethylsulfonyl)-N-(3-phenyl-propyl)-D-α-aminobutanamide, monohydrochloride

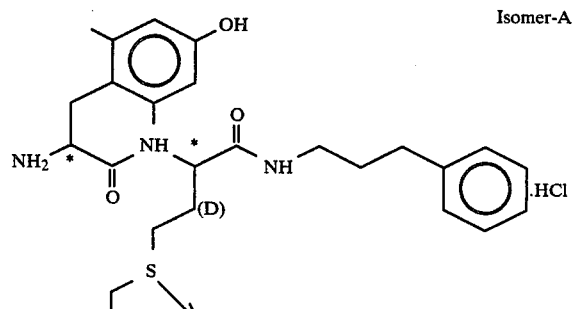

(2,6Me₂Tyr—(D)Eet(O₂)—NH(CH₂)₃Ph.HCl)

The title material is synthesized from the product of Example 21 by the method of Example 5.

EXAMPLE 26

2,6-dimethyltyrosyl-α-(ethylsulfonyl)-N-(3-phenyl-propyl)-D-α-aminobutanamide, monohydrochloride

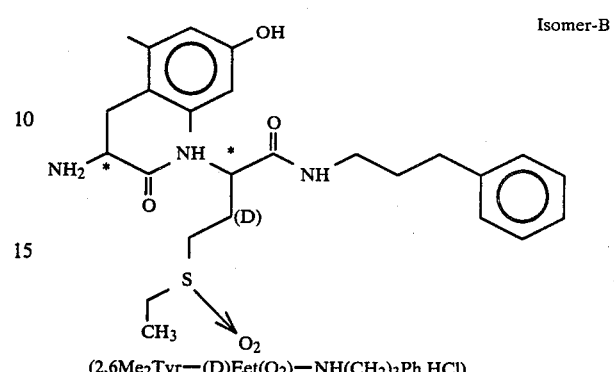

(2,6Me₂Tyr—(D)Eet(O₂)—NH(CH₂)₃Ph.HCl)

The title material is synthesized from the product of Example 22 by the method of Example 5.

EXAMPLE 27

1,1-dimethylethyl[3-(methylthio)-1R-[[(3-cyclohexyl-propyl)amino]carbonyl]propyl]carbamate

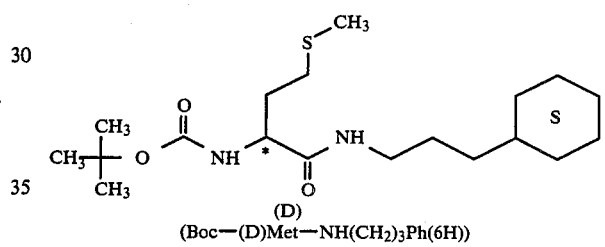

(Boc—(D)Met—NH(CH₂)₃Ph(6H))

The title material was prepared by the method of Example 18 using Boc-(D)Met in place of Boc-(D)Eet and NH₂(CH₂)₃Ph(6H) in place of NH₂(CH₂)₃Ph.

Optical rotation $[\alpha]_D$ +0.9°; +24.0° (365) CHCl₃.

Analysis Calcd. for $C_{19}H_{36}N_2O_3S$ (MW=372.57): C, 61.25; H, 9.74; N, 7.52; S, 8.61. Found: C, 61.05; H, 9.53; N, 7.45; S, 8.91.

EXAMPLE 28

2R-amino-N-(3-cyclohexylpropyl)-4-(methylthio)-butanamide

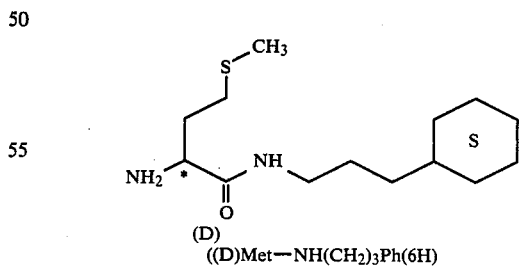

((D)Met—NH(CH₂)₃Ph(6H))

The HCl salt of the title material was prepared from the title compound of Example 27 by the method of Example 4. This material was stirred with a mixture of 5% NaHCO₃ sufficient to give a final aqueous pH of 8 and CH₂Cl₂. The organic layer was separated, washed with brine, dried (Na₂SO₄), and stripped of all solvent under reduced pressure to give the title material as a viscous oil.

Optical rotation [α], +10.4°; +43.1° (365) CHCl₃.

Analysis Calcd. for C₁₄H₂₈N₂OS (MW=272.45): C, 61.72; H, 10.35; N, 10.78; S, 11.77. Found: C, 61.70; H, 10.05; N, 10.53; S, 11.82.

EXAMPLE 29

N-[(1,1-dimethylethoxy)carbonyl]-2,6-dimethyltyrosyl-N-(3-cyclohexylpropyl)-D-methioninamide

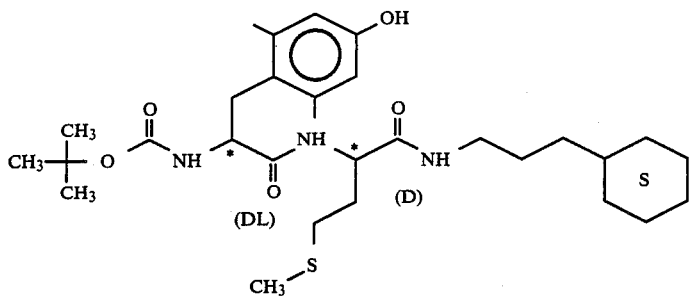

(Boc—(DL)2,6Me₂Tyr—(D)Met—NH(CH₂)₃Ph(6H))

The title mixture of diastereomers (isomers A & B) was prepared by the method of Example 1 using the title material of Example 28 in place of (D)Met-OMe and racemic Boc-2,6Me₂Tyr in place of Boc-Tyr and separated by PLC.

Diastereomer A [α]_D +15.7°; +88.7° (365) MeOH.

Analysis Calc. for C₃₀H₄₉N₃O₅S (MW=563.94): C, 63.91; H, 8.76; N, 7.45; S, 5.69. Found: C, 63.52; H, 8.50; N, 7.17; S, 5.75.

Diastereomer B [α]_D +40.0°; +149.9° (365) MeOH.

Analysis Calc. for C₃₀H₄₉N₃O₅S (MW=563.94): C, 63.91; H, 8.76; N, 7.45; S, 5.69. Found: C, 61.24; H, 8.33; N, 8.05; S, 6.60.

EXAMPLE 30

2,6-dimethyltyrosyl-N-(3-cyclohexylpropyl)-D-methioninamide, monohydrochloride

Isomer-A

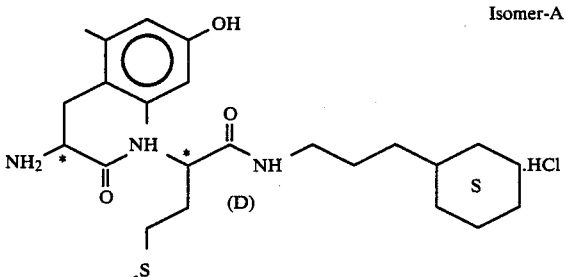

(2,6Me₂Tyr—(D)Met—NH(CH₂)₃(Ph(6H).HCl)

The title compound was prepared from diastereomer A of Example 29 by the method of Example 4.

Optical rotation [α]_D +31.7°; +180.8° (365) MeOH.

Analysis Calcd. for C₂₅H₄₂N₃O₃SCl.½H₂O (MW=509.14): C, 58.98; H, 8.51; N, 8.25; S, 6.30; Cl, 6.96. Found: C, 58.63; H, 8.22; N, 8.13; S, 6.50; Cl, 7.40.

EXAMPLE 31

2,6-dimethyltyrosyl-N-(3-cyclohexylpropyl)-D-methioninamide, monohydrochloride

Isomer-B

Isomers-A + B

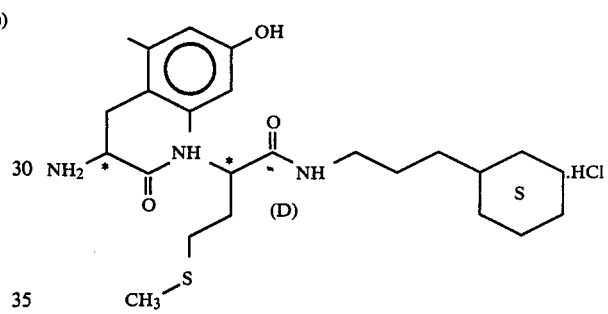

(2,6Me₂Tyr—(D)Met—NH(CH₂)₃Ph(6H).HCl)

The title compound was prepared from diastereomer B of Example 29 by the method of Example 4.

Optical rotation [α]_D +110.5°; +385.3° (365) MeOH.

Analysis calcd. for C₂₅H₄₂N₃O₃SCl.¼H₂O (MW=504.64): C, 59.50; H, 8.49; N, 8.33; S, 6.35; Cl, 7.02. Found: C, 59.59; H, 8.45; N, 8.28; S, 6.20; Cl, 7.02.

EXAMPLE 32

2,6-dimethyltyrosyl-N-(3-cyclohexylpropyl)-γ-(methylsulfinyl)-D-α-aminobutanamide, monohydrochloride Isomer-A

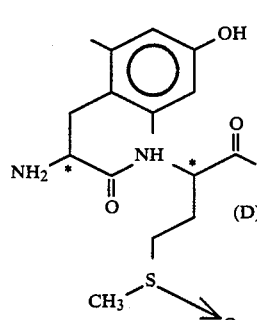

(2,6Me₂Tyr—(D)Met(O)—(D)Met(O)—NH(CH₂)₃Ph(6H).HCl)

The title compound was prepared from the product of Example 30 by the method of Example 16.

Optical rotation [α]_D −41.3°; −170.0° (365) MeOH.

Analysis calcd. for $C_{25}H_{42}N_3O_4SCl \cdot \frac{1}{2}H_2O$ (MW=525.14): C, 57.18; H, 8.25; N, 8.00; S, 6.10; Cl, 6.75. Found: C, 56.95; H, 8.05; N, 7.87; S, 6.31; Cl, 6.85.

EXAMPLE 33

2,6-dimethyltyrosyl-N-(3-cyclohexylpropyl)-γ-(methylsulfinyl)-D-α-aminobutanamide, monohydrochloride

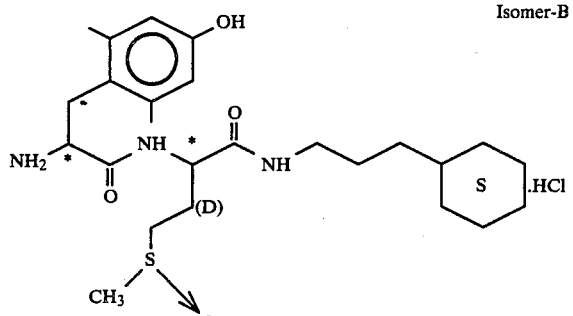

(2,6Me₂Tyr—(D)Met(O)—NH(CH₂)₃Ph(6H).HCl)

The title compound was prepared from the product of Example 31 by the method of Example 16.

Optical rotation $[\alpha]_D$ +91.6°; +316.8° (365) MeOH.
Analysis Calcd. for $C_{25}H_{42}N_3O_4SCl \cdot \frac{1}{2}H_2O$ (MW=525.14) C, 57.18; H, 8.25; N, 8.00; S, 6.10; Cl, 6.75. Found: C, 57.47; H, 8.12; N, 7.93; S, 6.04; Cl, 6.65.

EXAMPLE 34

2,6-dimethyltyrosyl-N-(3-cyclohexylpropyl)-α-(methylsulfonyl)-D-α-aminobutanamide, monohydrochloride

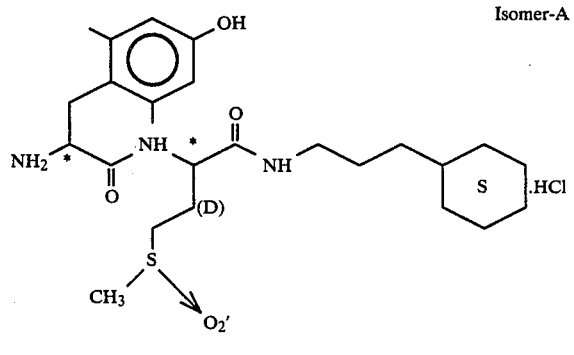

(2,6Me₂Tyr—(D)Met(O₂)—NH(CH₂)₃Ph(6H).HCl)

The title compound is synthesized from the title material of Example 30 by the method of Example 5.

EXAMPLE 35

2,6-dimethyltyrosyl-N-(3-cyclohexylpropyl)-γ-(methylsulfonyl)-D-α-aminobutanamide, monohydrochloride

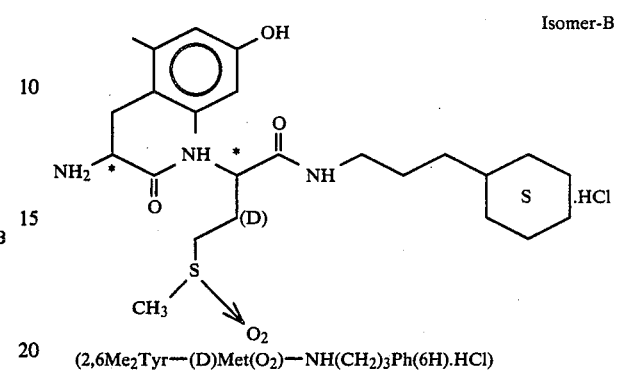

(2,6Me₂Tyr—(D)Met(O₂)—NH(CH₂)₃Ph(6H).HCl)

The title material is synthesized from the title material of Example 31 by the method of Example 5.

EXAMPLE 36

1,1-dimethylethyl[3-(methylthio)-1R-[[[3-(2-thienyl)propyl]amino]carbonyl]propyl]carbamate

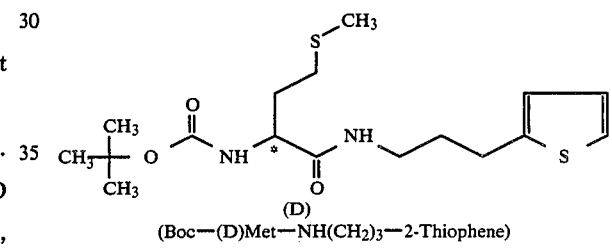

(Boc—(D)Met—NH(CH₂)₃—2-Thiophene)

The title material was prepared by the method of Example 18 using Boc-(D)Met in place of Boc-(D)Eet and NH₂(CH₂)₃-2-Thiophene in place of NH₂(CH₂)₃Ph.

Optical rotation $[\alpha]_D$ +0.9°; +21.8° (365) CHCl₃.
Analysis Calcd. for $C_{17}H_{28}N_2O_3S_2$ (MW=372.55): C, 54.81; H, 7.58; N, 7.52; S, 17.21. Found: C, 54.81; H, 7.61; N, 7.45; S, 17.07.

Example 37

2R-amino-4-(methylthio)-N-[3-(2-thienyl)propyl]butanamide

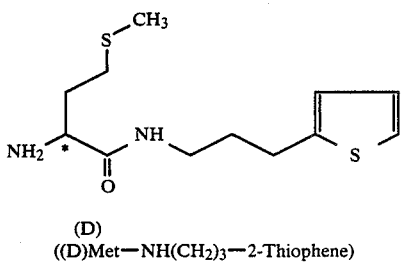

((D)Met—NH(CH₂)₃—2-Thiophene)

The title compound was synthesized from the title compound of Example 36 by the method of Example 28.

Optical rotation $[\alpha]_D$ +21.8°; +59.1° (365) CHCl₃.

Analysis Calcd. for $C_{12}H_{20}N_2OS_2 \cdot \frac{1}{2}H_2O$ (MW=281.44): C, 51.21; H, 7.52; N, 9.95; S, 22.78. Found: C, 51.65; H, 7.35; N, 9.99; S, 22.58.

Example 38

N-[(1,1-dimethylethoxy)carbonyl]-2,6-dimethyl-DL-tyrosyl-N-[3-(2-thienyl)propyl]-D-methioninamide

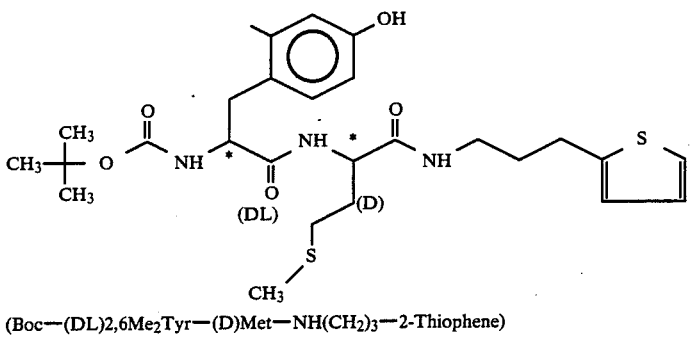

(Boc—(DL)2,6Me₂Tyr—(D)Met—NH(CH₂)₃—2-Thiophene)

The title mixture of diastereomers (isomers A and B) was prepared by the method of Example 1 using the title method of Example 37 in place of (D)Met-OMe and Boc-2,6Me₂Tyr in place of Boc-Tyr and separated by PLC.

Diastereomer A $[\alpha]_D$ +8.7°; +40.9° (365) CHCl₃.
Analysis Calcd. for $C_{28}H_{41}N_3O_5S_2$ (MW=563.78): C, 59.65; H, 7.33; N, 7.45; S, 11.38. Found: C, 59.59; H, 7.48; N, 7.24; S, 11.24.

Diastereomer B $[\alpha]_D$ +48.6°; +181.9° (365) CHCl₃.
Analysis Calcd. for $C_{28}H_{41}N_3O_5S_2$ (MW=513.78): C, 59.65; H, 7.33; N, 7.45; S, 11.38. Found: C, 59.29; H, 7.22; N, 7.61; S, 11.40.

Example 39

2,6-dimethyltyrosyl-N-[3-(2-thienyl)propyl]-D-methioninamide, monohydrochloride

Isomer-A

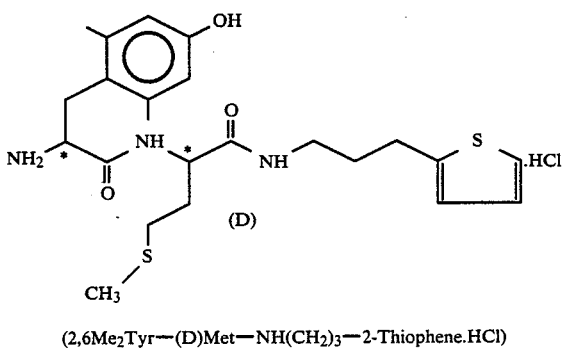

(2,6Me₂Tyr—(D)Met—NH(CH₂)₃—2-Thiophene.HCl)

The title compound was prepared from diastereomer A of Example 38 by the method of Example 4.
Optical rotation $[\alpha]_D$ −59.1°; −205.2° (365) MeOH
Analysis Calc. for $C_{23}H_{34}N_3O_3S_2Cl \cdot \frac{1}{4}H_2O$ (MW=504.61): C, 54.75; H, 6.89; N, 8.33; S, 12.71; Cl, 7.03. Found: C, 54.77; H, 6.80; N, 8.50; S, 12.61; Cl, 7.36.

Example 40

2,6-dimethyltyrosyl-N-[3-(2-thienyl)propyl]-D-methioninamide, monohydrochloride

Isomer-B

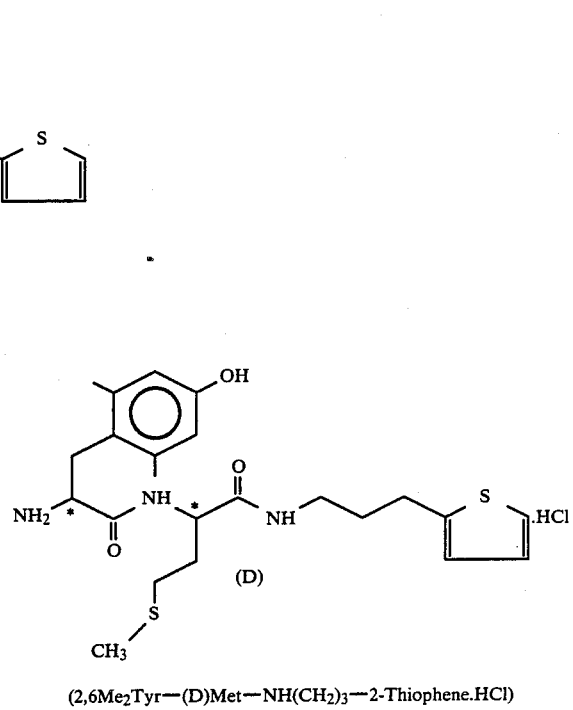

(2,6Me₂Tyr—(D)Met—NH(CH₂)₃—2-Thiophene.HCl)

The title compound was prepared from the B diastereomer of Example 38 by the method of Example 4.
Optical rotation $[\alpha]_D$ ±106.7°; +390.5° (365) MeOH.
Analysis Calc. for $C_{23}H_{34}N_3O_3S_2Cl \cdot \frac{1}{4}H_2O$ (MW=504.61): C, 54.75; H, 6.89; N, 8.33; S, 12.71; Cl, 7.03. Found: C, 54.77; H, 6.80; N, 8.50; S, 12.61; Cl, 7.36.

Example 41

2,6-dimethyltyrosyl-γ-(methylsulfinyl)-N-[3-(2-thienyl)propyl]-D-α-aminobutanamide, monohydrochloride Isomer-A

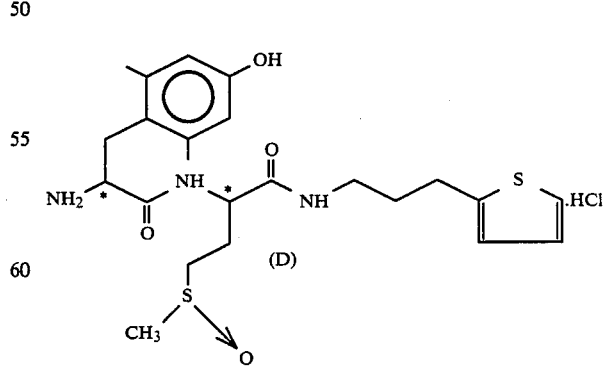

(2,6Me₂Tyr—(D)Met(O)—NH(CH₂)₃—2-Thiophene.HCl)

The title compound was synthesized from the product of Example 39 by the method of Example 16.

Optical rotation $[\alpha]_D$ −62.7°; −206.4° (365) MeOH.

Analysis Calc. for $C_{23}H_{34}N_3O_4S_2Cl \cdot \frac{1}{2}H_2O$ (MW=520.61): C, 53.06 H, 6.68; N, 8.07; S, 12.31; Cl, 6.81. Found: C, 52.93; H, 6.57; N, 7.97; S, 14.71; Cl, 6.84.

Example 42

2,6-dimethyltyrosyl-γ-(methylsulfinyl)-N-[3-(2-thienyl)propyl]-D-α-aminobutanamide, monohydrochloride Isomer-B

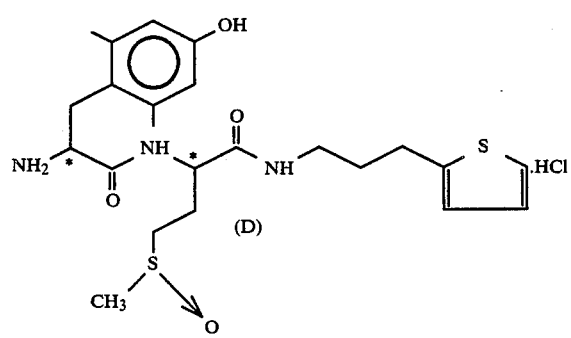

(2,6Me$_2$Tyr—(D)Met(O)—NH(CH$_2$)$_3$—2-Thiophene.HCl)

The title compound was synthesized from the product of Example 40 by the method of Example 16.

Optical rotation $[\alpha]$ +83.6°, +308.2° (365) MeOH.

Analysis Calc. for $C_{23}H_{34}N_3O_4S_2Cl \cdot \frac{1}{2}H_2O$ (525.12): C, 52.61; H, 6.72; N, 8.00; S, 12.21; Cl, 6.75. Found: C, 52.24; N, 6.43; N, 7.94; S, 12.32; Cl, 6.89.

Example 43

2,6-dimethyltyrosyl-γ-(methylsulfonyl)-N-[3-(2-thienyl)propyl]-D-α-aminobutanamide, monohydrochloride Isomer-A

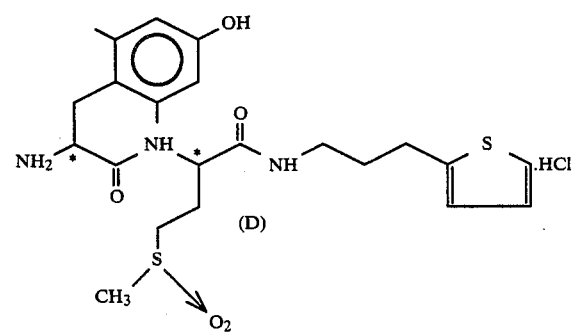

(2,6Me$_2$Tyr—(D)Met(O$_2$)—NH(CH$_2$)$_3$—2-Thiophene.HCl)

The title compound is prepared from the product of Example 39 by the method of Example 5.

Example 44

2,6-dimethyltyrosyl-γ-(methylsulfonyl)-N-[3-(2-thienyl)propyl]-D-α-aminobutanamide, monohydrochloride Isomer-B

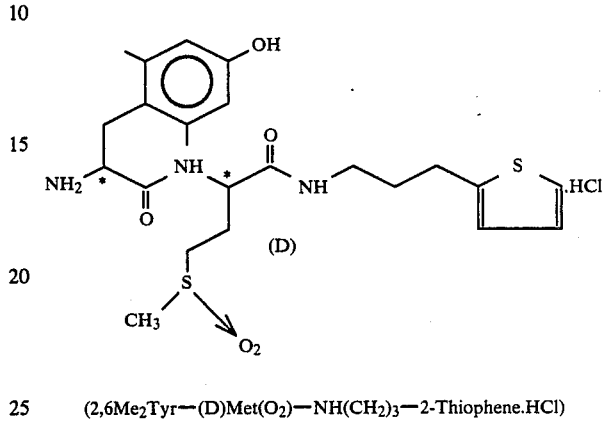

(2,6Me$_2$Tyr—(D)Met(O$_2$)—NH(CH$_2$)$_3$—2-Thiophene.HCl)

The title compound is prepared from the product of Example 40 by the method of Example 5.

Example 45

1,1-dimethylethyl[-4-[[(3-phenylpropyl)amino]carbonyl]-2H-thiopyran-4-yl]carbamate

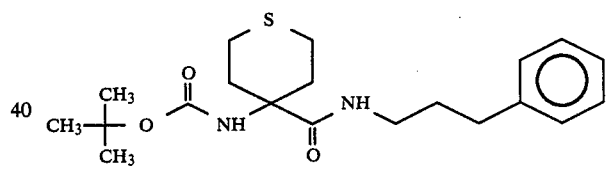

(Boc—cyc(6)Eet—NH(CH$_2$)$_3$Ph)

The title compound is prepared by the method of Example 18 using Boc-cyc(6)Eet in place of Boc-(D)Eet.

Example 46

4-aminotetrahydro-N-(3-phenylpropyl)-2H-thiopyran-4-carboxamide, monohydrochloride

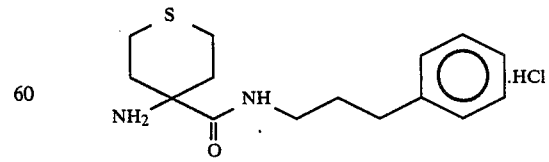

(Cyc(6)Eet—NH(CH$_2$)$_3$Ph.HCl)

The title compound is prepared from the title product of Example 45 by the method of Example 4.

Example 47

1,1-dimethylethyl[1-[(4-hydroxy-2,6-dimethylphenyl)methyl]-2-oxo-2-[[tetrahydro-4-[[(3-phenylpropyl)amino]carbonyl]-2H-thiopyran-4-yl]amino]ethyl]carbamate

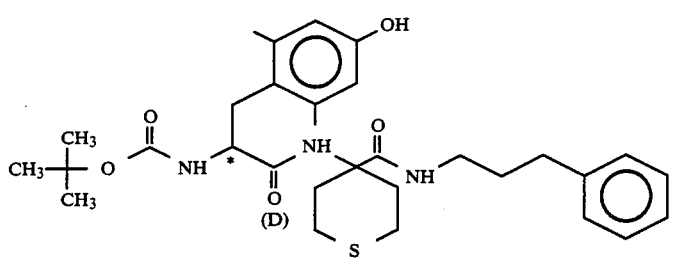

(Boc—2,6Me₂Tyr—cyc(6)Eet—NH(CH₂)₃Ph)

The title material is prepared by the method of Example 1 using the title material of Example 46 in place of (D)Met-OMe and Boc-2,6Me₂Tyr in place of Boc-Tyr.

Example 48

4-[[2-amino-3-(4-hydroxy-2,6-dimethylphenyl)-1-oxopropyl]amino]tetrahydro-N-(3-phenylpropyl)-2H-thiopyran-4-carboxamide, monohydrochloride

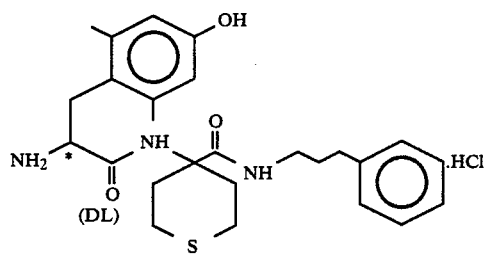

(2,6Me₂Tyr—cyc(6)Eet—NH(CH₂)₃Ph.HCl)

The title compound is prepared by the method of Example 4 from the product of Example 47.

Example 49

4-[[2-amino-3-(4-hydroxy-2,6-dimethylphenyl)-1-oxopropyl]amino]tetrahydro-N-(3-phenylpropyl)-2H-thiopyran-4-carboxamide, 1-oxide, monohydrochloride

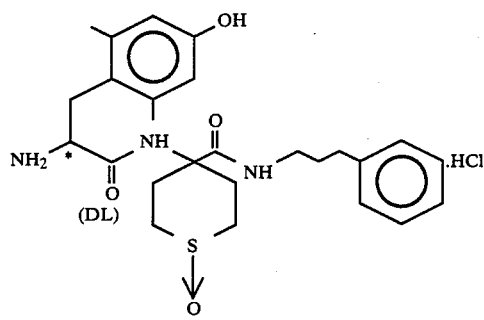

(2,6Me₂Tyr—cyc(6)Eet(O)—NH(CH₂)₃Ph.HCl)

The title material is obtained from the title material of Example 48 by the method of Example 16.

Example 50

4-[[2-amino-3-(4-hydroxy-2,6-dimethylphenyl)-1-oxopropyl]amino]tetrahydro-N-(3-phenylpropyl)-2H-thiopyran-4-carboxamide, 1,1-dioxide, monohydrochloride

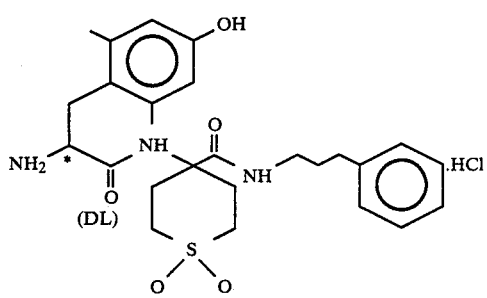

(2,6Me₂Tyr—cyc(6)Eet(O₂)—NH(CH₂)₃Ph.HCl)

The title material is prepared from the title compound of Example 48 by the method of Example 5.

Example 51

1,1-dimethylethyl[1S-[(4-hydroxy-2,6-dimethylphenyl)-methyl]-2-oxo-2-[[tetrahydro-4-[[(3-phenylpropyl)amino]carbonyl]-2H-thiopyran-4-yl]amino]ethyl]carbamate

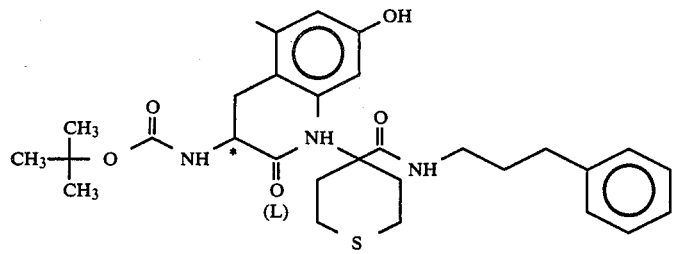

(Boc—2,6Me₂Tyr—cyc(6)Eet—NH(CH₂)₃Ph)

The title material is prepared by the method of Example 1 using the title material of Example 46 in place of (D)Met-OMe and Boc-(L)2,6Me₂Tyr in place of Boc-Tyr.

Example 52

4-[[2S-amino-3-(4-hydroxy-2,6-dimethylphenyl)-1-oxopropyl]amino]tetrahydro-N-(3-phenylpropyl)-2H-thiopyran-4-carboxamide, monohydrochloride

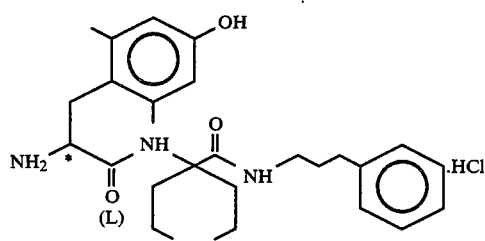

(2,6Me₂Tyr—cyc(6)Eet—NH(CH₂)₃Ph.HCl)

The title material is synthesized by the method of Example 4 from the title compound of Example 51.

Example 53

4-[[2S-amino-3-(4-hydroxy-2,6-dimethylphenyl)-1-oxopropyl]amino]tetrahydro-N-(3-phenylpropyl)-2H-thiopyran-4-carboxamide, 1-oxide, monohydrochloride

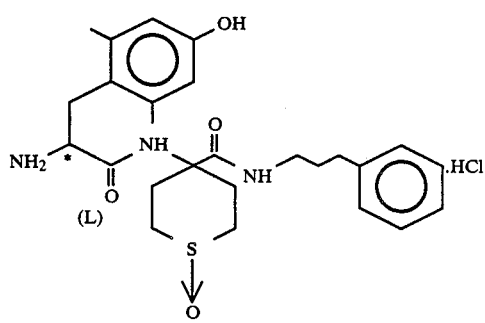

(2,6Me₂Tyr—cyc(6)Eet(O)—NH(CH₂)₃Ph.HCl)

The title compound is prepared from the product of Example 52 by the method of Example 16.

Example 54

4-[[2S-amino-3-(4-hydroxy-2,6-dimethylphenyl)-1-oxopropyl]amino]tetrahydro-N-(3-phenylpropyl)-2H-thiopyran-4-carboxamide, 1,1-dioxide, monohydrochloride

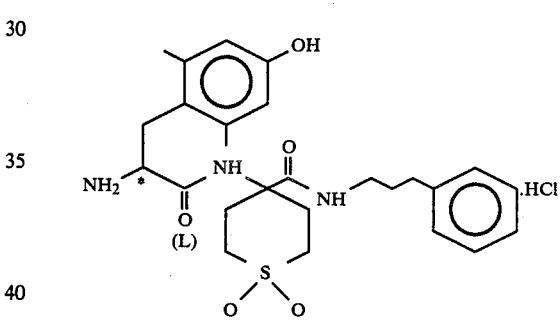

(2,6Me₂Tyr—cyc(6)Eet(O₂)—NH(CH₂)₃Ph.HCl)

The title material is synthesized from the title product of Example 52 by the method of Example 5.

Example 55

4-[[2R-amino-3-(4-hydroxy-2,6-dimethylphenyl)-1-oxopropyl]amino]tetrahydro-N-(3-phenylpropyl)-2H-thiopyran-4-carboxamide, monohydrochloride

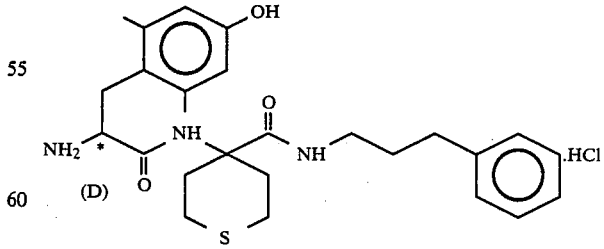

((D)2,6Me₂Tyr—cyc(6)Eet—NH(CH₂)₃Ph.HCl)

The title material is prepared by the method of Example 4 from a precursor similar to the title compound of Example 51 except a (D)2,6Me₂Tyr has replaced 2,6Me₂Tyr.

Example 56

4-[[2R-amino-3-(4-hydroxy-2,6-dimethylphenyl)-1-oxopropyl]amino]tetrahydro-N-(3-phenylpropyl)-2H-thiopyran-4-carboxamide, 1-oxide, monohydrochloride

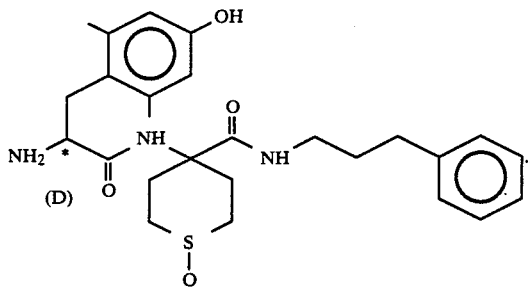

((D)2,6Me₂Tyr—cyc(6)Eet(O)—NH(CH₂)₃Ph.HCl)

The title compound is prepared from the title material of Example 55 by the method of Example 16.

Example 57

4-[[2R-amino-3-(4-hydroxy-2,6-dimethylphenyl)-1-oxopropyl]amino]tetrahydro-N-(3-phenylpropyl)-2H-thiopyran-4-carboxamide, 1,1-dioxide, monohydrochloride

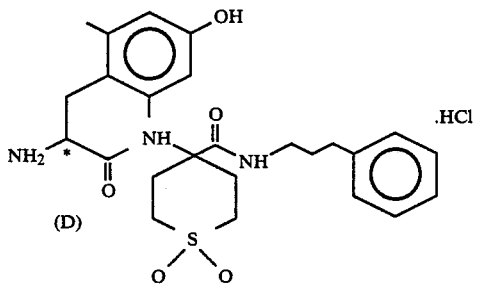

((D)2,6Me₂Tyr—cyc(6)Eet(O₂)—NH(CH₂)₃Ph.HCl)

The title material is synthesized from the title compound of Example 55 by the method of Example 5.

Example 58

1,1-dimethylethyl[tetrahydro-3-[[(3-phenylpropyl)amino]carbonyl]-3-thienyl]carbamate

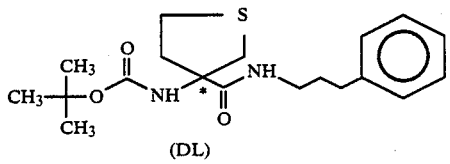

(Boc—cyc(5)Met—NH(CH₂)₃Ph)

The title material is prepared by the method of Example 18 using Boc-cyc(5)Met in place of Boc-Eet.

Example 59

3-aminotetrahydro-N-(3-phenylpropyl)-3-thiophenecarboxamide, monohydrochloride

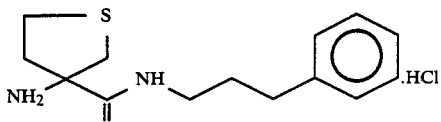

(cyc(5)Met—NH(CH₂)₃Ph.HCl)

The title compound is prepared from the title material of Example 58 by the method of Example 4.

Example 60

1,1-dimethylethyl N-[1-[(4-hydroxy-2,6-dimethylphenyl)methyl]-2-oxo-2-[[tetrahydro-3-[[(3-phenylpropyl)amino]carbonyl]-3-thienyl]amino]ethyl]carbamate

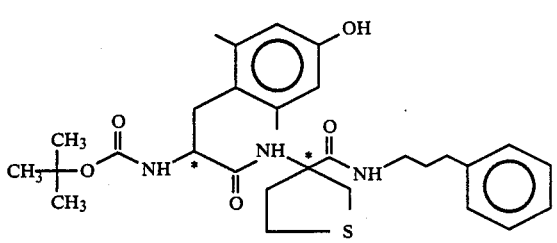

(Boc—2,6Me₂Tyr—cyc(5)Met—NH(CH₂)₃Ph)

The title mixtures of two enanteomeric pairs of isomers is prepared by the method of Example 1 using the title material of Example 59 in place of (D)Met-OMe and racemic Boc-2,6Me₂Tyr in place of Boc-Tyr. These isomeric pairs (isomers A and B) are separated by PLC.

Example 61

3-[[2-amino-3-(4-hydroxy-2,6-dimethylphenyl)-1-oxopropyl]amino]tetrahydro-N-(3-phenylpropyl)-3-thiophenecarboxamide, monohydrochloride Isomer-A

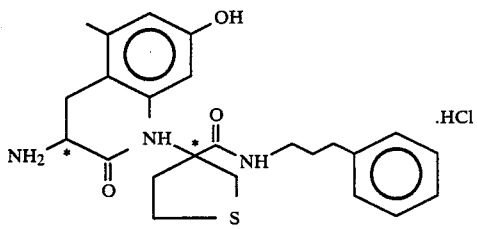

(2,6Me₂Tyr—cyc(5)Met—NH(CH₂)₃Ph.HCl)

The title material is prepared from enanteomeric mixture A of Example 60 by the method of Example 4.

Example 62

3-[[2-amino-3-(4-hydroxy-2,6-dimethylphenyl)-1-oxopropyl]amino]tetrahydro-N-(3-phenylpropyl)-3-thiophenecarboxamide, monohydrochloride Isomer-B

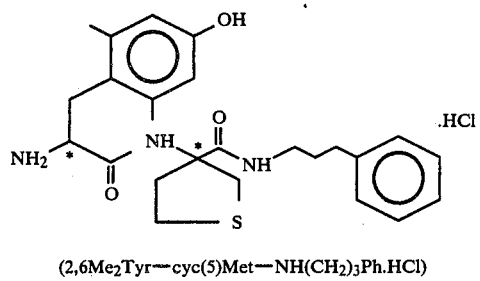

(2,6Me₂Tyr—cyc(5)Met—NH(CH₂)₃Ph.HCl)

The title compound is prepared from enanteomeric mixture B of Example 60 by the method of Example 4.

Example 63

3-[[2-amino-3-(4-hydroxy-2,6-dimethylphenyl)-1-oxopropyl]amino]tetrahydro-N-(3-phenylpropyl)-3-thiophenecarboxamide, 1-oxide, monohydrochloride Isomer-A

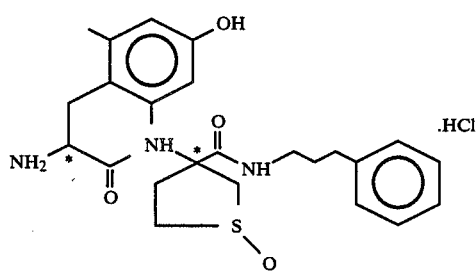

(2,6Me₂Tyr—Cyc(5)Met(O)—NH(CH₂)₃Phe.HCl)

The title compound is synthesized from the title product of Example 61 by the method of Example 16.

Example 64

3-[[2-amino-3-(4-hydroxy-2,6-dimethylphenyl)-1-oxopropyl]amino]tetrahydro-N-(3-phenylpropyl)-3-thiophenecarboxamide, 1-oxide, monohydrochloride Isomer-B

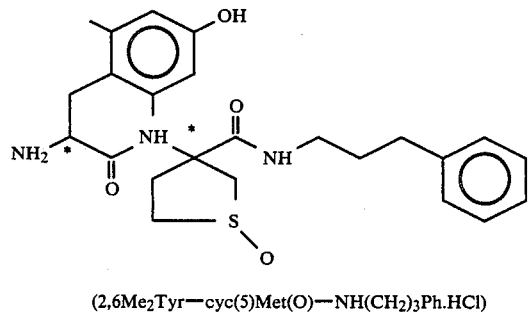

(2,6Me₂Tyr—cyc(5)Met(O)—NH(CH₂)₃Ph.HCl)

The title material is obtained from the title material of Example 62 by the method of Example 16.

Example 65

3-[[2-amino-3-(4-hydroxy-2,6-dimethylphenyl)-1-oxopropyl]amino]tetrahydro-N-(3-phenylpropyl)-3-thiophenecarboxamide, 1,1-dioxide, monohydrochloride Isomer-A

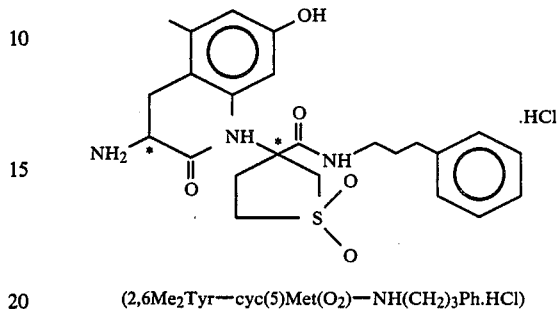

(2,6Me₂Tyr—cyc(5)Met(O₂)—NH(CH₂)₃Ph.HCl)

The title compound is prepared from the title material of Example 61 by the method of Example 5.

Example 66

3-[[2-amino-3-(4-hydroxy-2,6-dimethylphenyl)-1-oxopropyl]amino]tretrahydro-N-(3-phenylpropyl)-3-thiophenecarboxamide, 1,1-dioxide, monohydrochloride Isomer-B

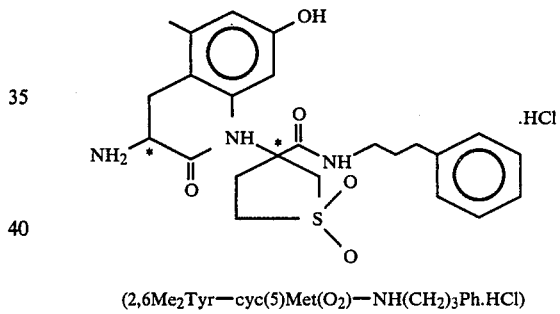

(2,6Me₂Tyr—cyc(5)Met(O₂)—NH(CH₂)₃Ph.HCl)

The title compound is synthesized from the title material of Example 62 by the method of Example 5.

Example 67

Isomer-A₁ and B₁ Series when x=0;

3-[[2S-amino-3-(4-hydroxy-2,6-dimethylphenyl)-1-oxopropyl]amino]tetrahydro-N-(3-phenylpropyl)-3-thiophenecarboxamide, monohydrochloride X=1, same except add 1-oxide;
X=2, same except add 1,1-dioxide.

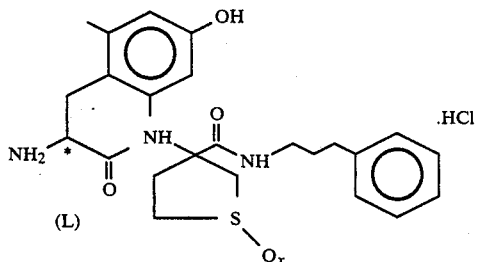

(L)

-continued

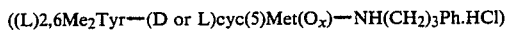
((L)2,6Me₂Tyr—(D or L)cyc(5)Met(Oₓ)—NH(CH₂)₃Ph.HCl)

All isomers of the above are prepared by use of Boc-(L)2,6Me₂Tyr in Example 60, separating diastereomers, and following procedures of Examples 61, 63 and 65 (x—0, 1, 2).

Example 68

IsoA₂ and B₂ when x=0;

3-[[2R-amino-3-(4-hydroxy-2,6-dimethylphenyl)-1-oxopropyl]mino]tetrahydro-N-(3-phenylpropyl)-3-thiophenecarboxamide, monohydrochloride, isomers A₂ and B₂;

X=1, same except add 1-oxide;
X=2, same except add 1,1-dioxide.

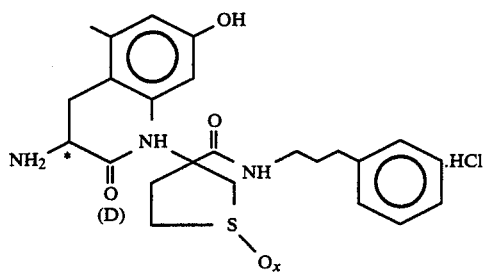

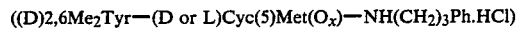
((D)2,6Me₂Tyr—(D or L)Cyc(5)Met(Oₓ)—NH(CH₂)₃Ph.HCl)

All isomers of the above are prepared by use of Boc(D)2,6Me₂Tyr in Example 60, separating the diastereomers, and treating the products as described by Examples 61, 63 and 65 (x=0, 1, 2).

Example 69

Analgesic properties of the substituted dipeptide amides

The receptor binding and biological properties of the following compounds of this invention are illustrated in Table 1 utilizing the previously described opiate binding and writhing assay. The standard screening dose for the writhing assay was 10 mg/kg s.c. and p.o. The standard screening dose for the opiate binding assay was $10^{-5}$ molar.

What is claimed is:

1. A compound of the formula:

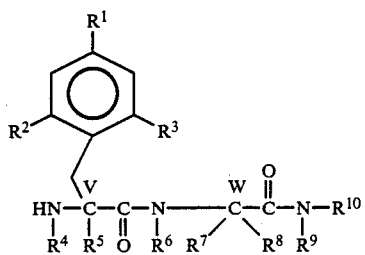

and the pharmaceutically acceptable acid addition salts thereof wherein $R^1$ is hydrogen, lower alkyl, hydroxy, lower alkoxy, —O(CH₂)ₙphenyl with the phenyl optionally substituted by halogen, —NO₂, —CN, —NH₂ or lower alkyl wherein n is 1 to 4; $R^2$ and $R^3$ represent lower alkyl, halogen, or lower alkoxy, or either one of $R^2$ or $R^3$ is hydrogen and the other lower alkyl, lower alkoxy or halogen; $R^4$, $R^5$, $R^6$, and $R^9$ may be the same or different and represent hydrogen, lower alkyl, cycloalkyl having 3 to 8 carbons, unsaturated lower alkyl, or (CH₂)ₘcycloalkyl with the cycloalkyl having 3 to 8 carbons and m is 1 to 4; $R^{10}$ is hydrogen or —(CH₂)ₚ-phenyl or with the phenyl optionally substituted with —NH₂, —OH, halogen, —NO₂, or lower alkyl or —(CH₂)ₚ thienyl wherein p is 1 to 4; one of $R^7$ or $R^8$ is —(CH₂)f—S(O)z—(CH₂)q—CH₃ where f is 1 to 3 and q is 0 to 3, z is 1, 1 or 2 and the other is hydrogen or lower alkyl, or $R^7$ and $R^8$ together with carbon w are

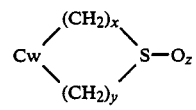

where
x and y are independently 1 to 3 and z is 0, 1 or 2;
V represents an asymmetric carbon that may be racemic or have the D or L configuration;
W represents an asymmetric carbon when $R^7$ and $R^8$ are not the same that may be racemic or have the D or L configuration.

2. A compound according to claim 1 of the formula

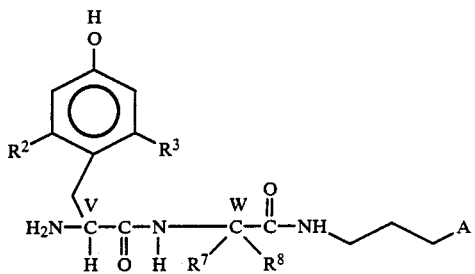

and the pharmaceutically acceptable acid addition salts thereof, wherein A is phenyl, thienyl or cyclohexyl; wherein $R^2$ and $R^3$ are methyl; and wherein one of $R^7$ or $R^8$ is —(CH₂)f—S(O)z—(CH₂)q—CH₃ where f is 1 to 3 and q is 0 to 3, z is 0, 1 or 2 and the other is hydrogen or lower alkyl or $R^7$ and $R^8$ together with carbon w are

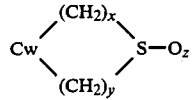

where
x and y are independently 1 to 3 and z is 0, 1 or 2;
V represents an asymmetric carbon that may be racemic or have the D or L configuration;
W represents an asymmetric carbon when $R^7$ and $R^8$ are not the same that may be racemic or have the D or L configuration.

3. A compound according to claim 2, which is tyrosyl-N-(3-phenylpropyl)-D-methioninamide, hydrochloride.

4. A compound according to claim 2, which is tyrosyl-γ-(methylsulfonyl)-N-(3-phenylpropyl)-D-α-aminobutanamide, hydrochloride.

5. A compound according to claim 2, which is tyrosyl-N-(3-phenylpropyl)-DL-methioninamide, hydrochloride.

6. A compound according to claim 2, which is tyrosyl-δ-(methylsulfonyl)-N-(3-phenylpropyl)-DL-α-aminobutanamide, hydrochloride.

7. A compound according to claim 2, which is 2,6-dimethyltyrosyl-N-(3-phenylpropyl)-D-methioninamide, hydrochloride.

8. A compound according to claim 2, which is 2,6-dimethyltyrosyl-α-(methylsulfinyl)-N-(3-phenylpropyl)-D-α-aminobutanamide, hydrochloride.

9. A compound according to claim 2, which is 2,6-dimethyltyrosyl-S-ethyl-N-(3-phenylpropyl)-D-homocysteinamide, hydrochloride.

10. A compound according to claim 2, which is 2,6-dimethyltyrosyl-δ-(ethylsulfinyl)-N-(3-phenylpropyl)-D-α-aminobutanamide, hydrochloride.

11. A compound according to claim 2, which is 2,6-dimethyltyrosyl-γ-(ethylsulfonyl)-N-(3-phenylpropyl)-D-α-aminobutanamide, hydrochloride.

12. A compound according to claim 2, which is 2,6-dimethyltyrosyl-N-(3-cyclohexylpropyl)-D-methioninamide, hydrochloride.

13. A compound according to claim 2, which is 2,6-dimethyltyrosyl-N-(3-cyclohexylpropyl)-γ-(methylsulfinyl)-D-α-aminobutanamide, hydrochloride.

14. A compound according to claim 2, which is 2,6-dimethyltyrosyl-N-(3-cyclohexylpropyl)-γ-(methylsulfonyl)-D-α-aminobutanamide, hydrochloride.

15. A compound according to claim 2, which is 2,6-dimethyltyrosyl-N-[3-(2-thienyl)propyl]-D-methioninamide, hydrochloride.

16. A compound according to claim 2, which is 2,6-dimethyltyrosyl-γ-(methylsulfinyl)-N-[3-(2-thienyl)propyl]-D-α-aminobutanamide, hydrochloride.

17. A compound according to claim 2, which is 2,6-dimethyltyrosyl-γ-(methylsulfonyl)-N-[3-(2-thienyl)propyl]-D-α-aminobutanamide, hydrochloride.

18. A compound according to claim 2, which is 4-[[2-amino-3-(4-hydroxy-2,6-dimethylphenyl)-1-oxopropyl]amino]tetrahydro-N-(3-phenylpropyl)-2H-thiopyran-4-carboxamide, hydrochloride.

19. A compound according to claim 1, which is 4-[[2-amino-3-(4-hydroxy-2,6-dimethylphenyl)-1-oxopropyl]amino]tetrahydro-N-(3-phenylpropyl)-2H-thiopyran-4-carboxamide, 1-oxide, hydrochloride.

20. A compound according to claim 1, which is 4-[[2-amino-3-(4-hydroxy-2,6-dimethylphenyl)-1-oxopropyl]amino]tetrahydro-N-(3-phenylpropyl)-2H-thiopyran-4-carboxamide, 1,1-dioxide, hydrochloride.

21. A compound according to claim 1, which is 4-[[2S-amino-3-(4-hydroxy-2,6-dimethylphenyl)-1-oxopropyl]amino]tetrahydro-N-(3-phenylpropyl)-2H-thiopyran-4-carboxamide, 1-oxide, hydrochloride.

22. A compound according to claim 2, which is 4-[[2S-amino-3-(4-hydroxy-2,6-dimethylphenyl)-1-oxopropyl]amino]tetrahydro-N-(3-phenylpropyl)-2H-thiopyran-4-carboxamide, 1,1-dioxide, hydrochloride.

23. A compound according to claim 2, which is 4-[[2R-amino-3-(4-hydroxy-2,6-dimethylphenyl)-1-oxopropyl]amino]tetrahydro-N-(3-phenylpropyl)-2H-thiopyran-4-carboxamide, hydrochloride.

24. A compound according to claim 1, which is 4-[[2R-amino-3-(4-hydroxy-2,6-dimethylphenyl)-1-oxopropyl]amino]tetrahydro-N-(3-phenylpropyl)-2H-thiopyran-4-carboxamide, 1-oxide, hydrochloride.

25. A compound according to claim 2, which is 4-[[2R-amino-3-(4-hydroxy-2,6-dimethylphenyl)-1-oxopropyl]amino]tetrahydro-N-(3-phenylpropyl)-2H-thiopyran-4-carboxamide, 1,1-dioxide, hydrochloride.

26. A compound according to claim 2, which is 3-[[2-amino-3-(4-hydroxy-2,6-dimethylphenyl)-1-oxopropyl]amino]tetrahydro-N-(3-phenylpropyl)-3-thiophenecarboxamide, hydrochloride.

27. A compound according to claim 2, which is 3-[[2-amino-3-(4-hydroxy-2,6-dimethylphenyl)-1-oxopropyl]amino]tetrahydro-N-(3-phenylpropyl)-3-thiophenecarboxamide, 1-oxide, hydrochloride.

28. A compound according to claim 2, which is 3-[[2-amino-3-(4-hydroxy-2,6-dimethylphenyl)-1-oxopropyl]amino]tetrahydro-N-(3-phenylpropyl)-3-thiophenecarboxamide, 1,1-dioxide, hydrochloride.

* * * * *

UNITED STATES PATENT AND TRADEMARK OFFICE
CERTIFICATE OF CORRECTION

PATENT NO. : 4,757,153

DATED : July 12, 1988

INVENTOR(S) : HANSEN JR., ET AL.

It is certified that error appears in the above-identified patent and that said Letters Patent is hereby corrected as shown below:

Column 4, line 47, reading "crystallization of column" should read -- crystallization or column --.

Column 10, to the right of the first structure, reading

This error regarding the misplacement of the dot (.) occurs in various situations throughout the remainder of the patent.

Column 10, line 37, reading "-D-$\gamma$-" should read -- -D-$\alpha$--.

Column 12, the second structure, that portion of the structure reading

Column 13, the first structure, that portion of the structure reading

Column 13, the second structure, that portion of the structure reading

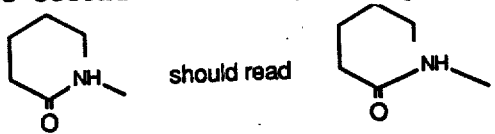

Column 15, the following was omitted and should be inserted above the second structure: --Isomer-B--.

Column 17, the first structure, that portion of the structure reading

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 17, the second structure, that portion of the structure reading

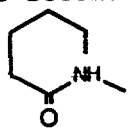 should read 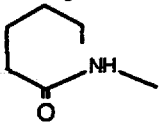

Column 18, the first structure, that portion of the structure reading

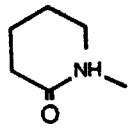 should read 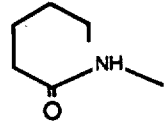

Column 18, the second structure, that portion of the structure reading

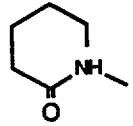 should read 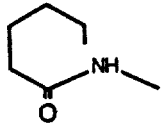

Column 19, the first structure, that portion of the structure reading

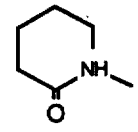 should read 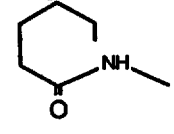

Column 19, the second structure, that portion of the structure reading

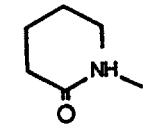 should read 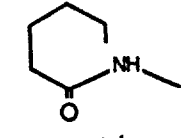

Column 20, the first structure, that portion of the structure reading

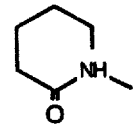 should read 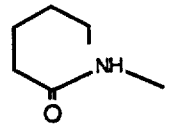

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 21, the first structure, that portion of the structure reading

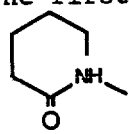 should read 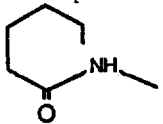

Column 21, the second structure, that portion of the structure reading

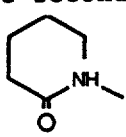 should read 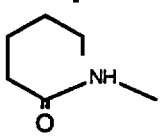

Column 22, the first structure, that portion of the structure reading

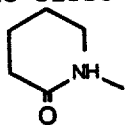 should read 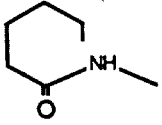

Column 22, the second structure, that portion of the structure reading

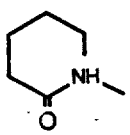 should read 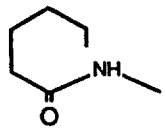

Column 22, line 64, reading "-(D)Met(O)-(D)Met(O)-" should read -- -(D)Met(O)- --.

Column 23, the first structure, that portion of the structure reading

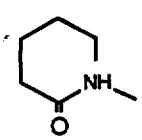 should read 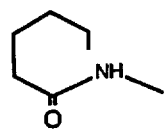

Column 23, line 44, reading "-(3-cyclohexylpropyl)-α-" should read -- -(3-cyclohexylpropyl)-δ- --.

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 23, the second structure, that portion of the structure reading

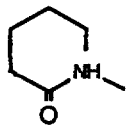 should read 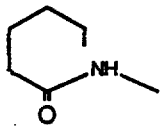

Column 24, the first structure, that portion of the structure reading

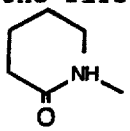 should read 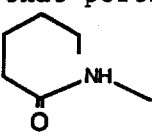

Column 25, the first structure, that portion of the structure reading

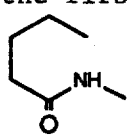 should read 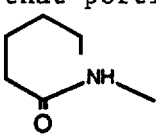

Column 25, the second structure, that portion of the structure reading

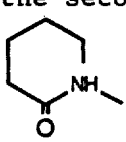 should read 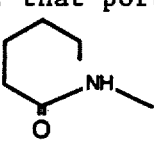

Column 26, the first structure, that portion of the structure reading

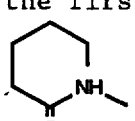 should read 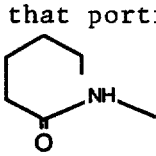

Column 26, the second structure, that portion of the structure reading

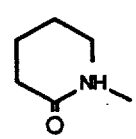 should read 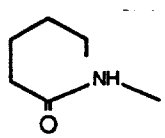

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 27, the first structure, that portion of the structure reading

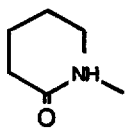 should read 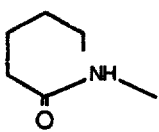

Column 27, the second structure, that portion of the structure reading

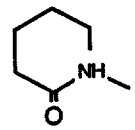 should read 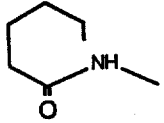

Column 28, the first structure, that portion of the structure reading

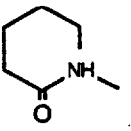 should read 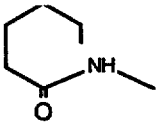

Column 29, the first structure, that portion of the structure reading

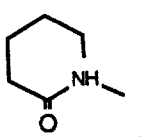 should read 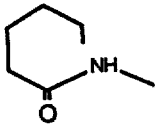

Column 29, the second structure, that portion of the structure reading

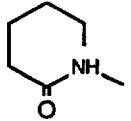 should read 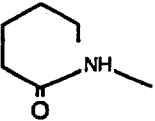

Column 29, the third structure, that portion of the structure reading

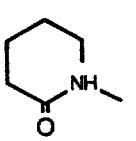 should read 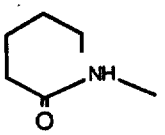

UNITED STATES PATENT AND TRADEMARK OFFICE
CERTIFICATE OF CORRECTION

PATENT NO. : 4,757,153
DATED : July 12, 1988
INVENTOR(S) : Hansen Jr., et al.

It is certified that error appears in the above-identified patent and that said Letters Patent is hereby corrected as shown below:

Column 30, the first structure, that portion of the structure reading

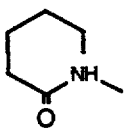 should read 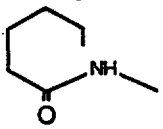

Column 31, the first structure, that portion of the structure reading

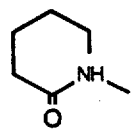 should read 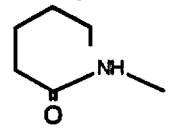

Column 31, the second structure, that portion of the structure reading

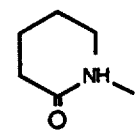 should read 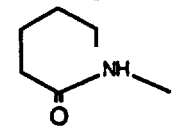

Column 31, the third structure, that portion of the structure reading

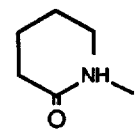 should read 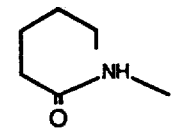

Column 32, the first structure, that portion of the structure reading

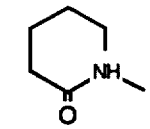 should read 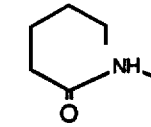

Column 32, the second structure, that portion of the structure reading

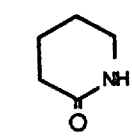 should read 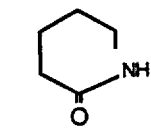

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 33, the first structure, that portion of the structure reading

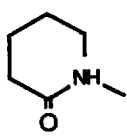 should read 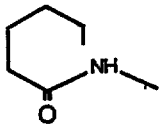

Column 33, the second structure, that portion of the structure reading

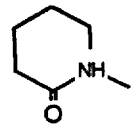 should read 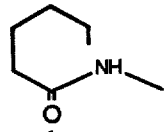

Column 34, the second structure, that portion of the structure reading

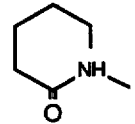 should read 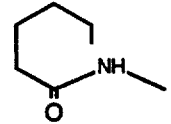

Column 34, the third structure, that portion of the structure reading

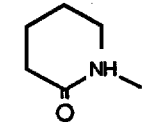 should read 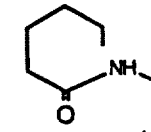

Column 35, the first structure, that portion of the structure reading

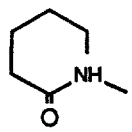 should read 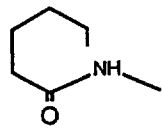

Column 35, the second structure, that portion of the structure reading

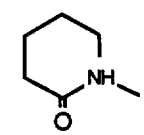 should read 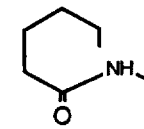

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 35, the third structure, that portion of the structure reading

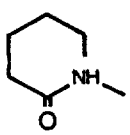   should read   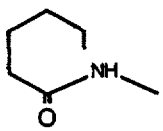

Column 36, the first structure, that portion of the structure reading

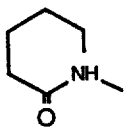   should read   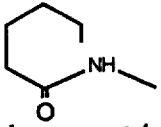

Column 36, the second structure, that portion of the structure reading

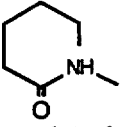   should read   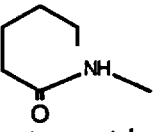

Column 36, the third structure, that portion of the structure reading

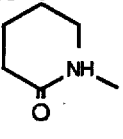   should read   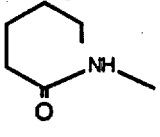

UNITED STATES PATENT AND TRADEMARK OFFICE
CERTIFICATE OF CORRECTION

PATENT NO. : 4,757,153

DATED : July 12, 1988

INVENTOR(S) : Hansen Jr., et al.

It is certified that error appears in the above-identified patent and that said Letters Patent is hereby corrected as shown below:

Column 37, the first structure, that portion of the structure reading

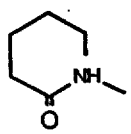 should read 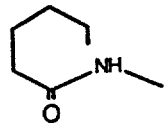

Signed and Sealed this

Third Day of April, 1990

Attest:

HARRY F. MANBECK, JR.

Attesting Officer

Commissioner of Patents and Trademarks